(12) United States Patent
Ratni et al.

(10) Patent No.: US 12,084,461 B2
(45) Date of Patent: Sep. 10, 2024

(54) BICYCLIC HETEROARYL DERIVATIVES

(71) Applicant: Hoffmann-La Roche Inc., Little Falls, NJ (US)

(72) Inventors: Hasane Ratni, Basel (CH); Jennifer Louise Carter, Virginia Water (GB)

(73) Assignee: Hoffmann-La Roche Inc., Little Falls, NJ (US)

( * ) Notice: Subject to any disclaimer, the term of this patent is extended or adjusted under 35 U.S.C. 154(b) by 643 days.

(21) Appl. No.: 17/273,278

(22) PCT Filed: Sep. 2, 2019

(86) PCT No.: PCT/EP2019/073303
§ 371 (c)(1),
(2) Date: Mar. 3, 2021

(87) PCT Pub. No.: WO2020/048904
PCT Pub. Date: Mar. 12, 2020

(65) Prior Publication Data
US 2021/0323980 A1    Oct. 21, 2021

(30) Foreign Application Priority Data

Sep. 3, 2018    (EP) ..................................... 18192219

(51) Int. Cl.
| | |
|---|---|
| *C07D 498/04* | (2006.01) |
| *A61K 31/5365* | (2006.01) |
| *A61P 25/28* | (2006.01) |
| *A61P 35/00* | (2006.01) |
| *C07D 519/00* | (2006.01) |

(52) U.S. Cl.
CPC ............ *C07D 519/00* (2013.01); *A61P 35/00* (2018.01)

(58) Field of Classification Search
CPC .... C07D 498/04; A61K 31/5365; A61P 25/28
See application file for complete search history.

(56) References Cited

U.S. PATENT DOCUMENTS

| | | |
|---|---|---|
| 7,875,611 B2 | 1/2011 | Bain et al. |
| 8,252,935 B2 | 8/2012 | Ho et al. |
| 8,486,967 B2 | 7/2013 | Baumann et al. |
| 8,673,900 B2 | 3/2014 | Zhu et al. |
| 8,703,753 B2 | 4/2014 | Sredni et al. |
| 8,703,763 B2 | 4/2014 | Baumann et al. |
| 8,754,100 B2 | 6/2014 | Kitazawa et al. |
| 8,891,284 B2 | 11/2014 | Williams et al. |
| 9,115,143 B2 | 8/2015 | Minne et al. |
| 9,637,491 B2 | 5/2017 | Almstetter et al. |
| 10,562,903 B2 | 2/2020 | Bartels et al. |
| 10,941,147 B2 | 3/2021 | Bartels et al. |
| 2005/0020481 A1 | 1/2005 | Bain et al. |
| 2005/0119315 A1 | 6/2005 | Fedida et al. |
| 2007/0004718 A1 | 1/2007 | Bain et al. |
| 2007/0190156 A1 | 8/2007 | Beatch et al. |
| 2008/0070911 A1 | 3/2008 | Bain et al. |
| 2010/0029639 A1 | 2/2010 | Bain et al. |
| 2011/0190269 A1 | 8/2011 | Baumann et al. |
| 2011/0207730 A1 | 8/2011 | Bain et al. |
| 2018/0237432 A1 | 8/2018 | Baumann et al. |

FOREIGN PATENT DOCUMENTS

| | | |
|---|---|---|
| CN | 103403003 | 11/2013 |
| CN | 107922437 | 4/2018 |
| CN | 108137579 | 6/2018 |
| WO | 1999/21560 | 5/1999 |
| WO | 2000/47547 | 8/2000 |
| WO | 00/71528 | 11/2000 |
| WO | 2001/32170 | 5/2001 |
| WO | 08/138753 | 11/2008 |
| WO | 2010/138901 A1 | 12/2010 |
| WO | 2011/092272 A1 | 8/2011 |
| WO | 2011/101304 A2 | 8/2011 |
| WO | 2012/116965 A1 | 9/2012 |
| WO | 2014/060112 A1 | 4/2014 |
| WO | 2017/042114 | 3/2017 |
| WO | 2018/001918 | 1/2018 |
| WO | 2018/060300 A1 | 4/2018 |

(Continued)

OTHER PUBLICATIONS

Kummerer, K., "Pharmaceuticals in the Environment" Ann Rev Environ Res 35:57-75 (Nov. 1, 2010).
Chowdhury et al., "Understanding the brain uptake and permeability of small molecules through the BBB: A technical overview" Journal of Cerebral Blood Flow & Metabolism (doi: 10.1177/0271678X20985946; PM ID: 33444097; PMCID: PMC8327119.), 41(8):1797-1820 (Jan. 14, 2021).
Ulrika Yngve et al., "Triazolopyrimidinones as g-secretase modulators: structure-activity relationship, modulator profile, and in vivo profiling" MedChemComm 4(2):422 (Jan. 1, 2013).
Steeg, P., et al., "Brain Metastases as Preventive and Theraputic Targets" Nat Rev Cancer 11(5):352-363 (Apr. 7, 2011).
"International Preliminary Report on Patentability—PCT/EP2019/084538" (Report Issuance Date: Jun. 8, 2021; Chapter I),:pp. 1-8 (Jun. 24, 2021).

(Continued)

*Primary Examiner* — Irina Neagu
(74) *Attorney, Agent, or Firm* — Vasily Ignatenko

(57) ABSTRACT

The invention provides new bicyclic heteroaryl compounds having the general formula (I) wherein $R^1$, Ar, n and m are as described herein, compositions including the compounds, processes of manufacturing the compounds and methods of using the compounds.

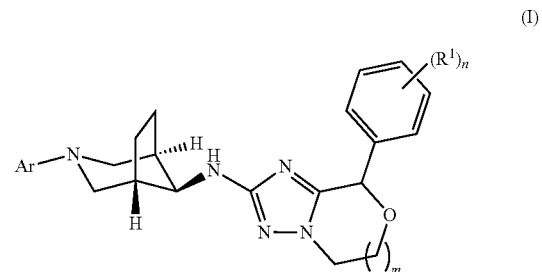

(I)

19 Claims, No Drawings

(56) References Cited

FOREIGN PATENT DOCUMENTS

| WO | 2018/083050 A1 | 5/2018 |
| WO | 2018/087018 | 5/2018 |
| WO | 2018/111926 | 6/2018 |
| WO | 2019/141832 | 7/2019 |

OTHER PUBLICATIONS

"International Search Report—PCT/EP2019/084538" (w/Written Opinion),:pp. 1-13 (Mar. 5, 2020).
"International Search Report—PCT/EP2019/073303" (w/Written Opinion),:pp. 1-12 (Oct. 7, 2019).
Belikov, V.G. "Pharmaceutical Chemistry," Tutorial, 4th, revised and expanded edition, Moscow, MEDPress-Inform, 2007, pp. 27-29 (including English Translation).
"International Preliminary Report on Patentability—PCT/EP2019/073303" (Report Issuance Date: Mar. 9, 2021, Chapter I),:pp. 1-8 (Mar. 18, 2021).
Mironov, A.N. et al.,:1-24 ( 2012).

BICYCLIC HETEROARYL DERIVATIVES

FIELD OF THE INVENTION

The present invention relates to bicyclic heteroaryl compounds useful as gamma-secretase modulators, their manufacture, pharmaceutical compositions comprising said compounds and their use as medicaments for the therapeutic and/or prophylactic treatment of diseases associated with the deposition of β-amyloid in the brain, such as Alzheimer's disease, cerebral amyloid angiopathy, hereditary cerebral hemorrhage with amyloidosis-Dutch type (HCHWA-D), multi-infarct dementia, dementia pugilistica and Down syndrome.

BACKGROUND OF THE INVENTION

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain lengths, e.g. Aβ38, Aβ40 and Aβ42. The latter one is regarded to be the more pathogenic amyloid peptide because of its strong tendency to form neurotoxic aggregates. β-Secretase is a typical aspartyl protease.

γ-Secretase is a high molecular weight complex that consists of four essential subunits: presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature, 525 (2015), 212-217). The presenilins are bearing the catalytic site and represent a group of atypical aspartyl proteases which cleave their substrates within the TM and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e. ablation of the presenilin genes, and by low-molecular weight inhibitory compounds. According to the amyloid cascade hypothesis for AD the production and deposition of Aβ is the ultimate cause for the disease. Therefore, it is believed that selective and potent inhibition of γ-secretase might be useful for the prevention and treatment of AD.

An alternative mode of treatment is the modulation of the γ-secretase activity which results in a selective reduction of the Aβ42 production. This would lead to an increase of shorter Aβ isoforms, such as Aβ38, Aβ37 or others, which have no or reduced capability for aggregation and plaque formation, and are not or less neurotoxic. Compounds modulating γ-secretase activity include certain non-steroidal anti-inflammatory drugs (NSAIDs) and related analogues (Weggen et al., Nature, 414 (2001) 212-216).

Numerous documents describe the current knowledge on γ-secretase modulation, such as the following publications:
Morihara et al., *J. Neurochem.*, 83 (2002), 1009-12
Jantzen et al., *J. Neuroscience*, 22 (2002), 226-54
Takahashi et al., *J. Biol. Chem.*, 278 (2003), 18644-70
Beher et al., *J. Biol. Chem.*, 279 (2004), 43419-26
Lleo et al., *Nature Med.*, 10 (2004), 1065-6
Kukar et al., *Nature Med.*, 11 (2005), 545-50
Perretto et al., *J. Med. Chem.*, 48 (2005), 5705-20
Clarke et al., *J. Biol. Chem.*, 281 (2006) 31279-89
Stock et al., *Bioorg. Med. Chem. Lett.*, 16 (2006) 2219-2223
Narlawar et al., *J. Med. Chem.*, 49 (2006) 7588-91
Ebke et al., *J. Biol. Chem.*, 286 (2011) 37181-86
Oehlich, Gijsen et al., *J. Med. Chem.*, 54 (2011), 669-698
Li et al., *Biochemistry*, 52 (2013), 3197-3216
Hall et al., *Progress in Med. Chem.*, 53 (2014) 101-145
Bursavich et al., *J. Med. Chem.*, 59 (2016).

Therefore, modulating the γ-secretase activity is a promising therapeutic strategy for the treatment or prevention of diseases associated with the deposition of β-amyloid in the brain, such as Alzheimer's disease, cerebral amyloid angiopathy, hereditary cerebral hemorrhage with amyloidosis-Dutch type (HCHWA-D), multi-infarct dementia, dementia pugilistica and Down syndrome.

There is a need for new compounds, formulations, treatments and therapies to treat diseases and disorders associated with the deposition of β-amyloid in the brain. It is, therefore, an object of this invention to provide compounds useful for the treatment or prevention or amelioration of such diseases and disorders with improved therapeutic properties.

SUMMARY OF THE INVENTION

A first object of the present invention is a compound of formula (I)

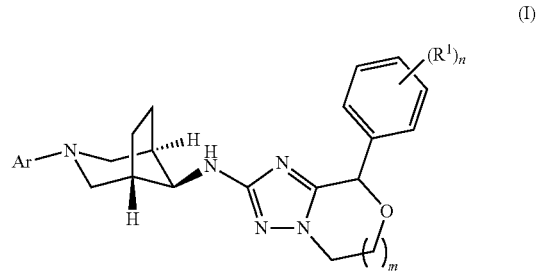

wherein
$R^1$ is halogen, lower alkyl, lower alkyl substituted by halogen, lower alkoxy, or lower alkoxy substituted by halogen,
and $R^1$ may be different if n=2 or 3;

m is 1 or 2;
n is 1, 2 or 3;
Ar is a six membered heteroaryl group, selected from

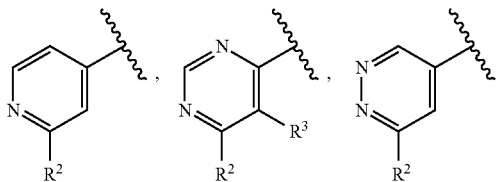

wherein
$R^2$ is hydrogen, halogen, lower alkyl, lower alkyl substituted by halogen, or lower alkoxy;
$R^3$ is hydrogen or halogen;
or a pharmaceutically acceptable salt thereof.

A further object of the invention is a process for the preparation of a compound of formula (I) as described herein, comprising reacting a compound 5

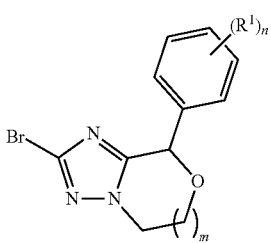

with an amine 6

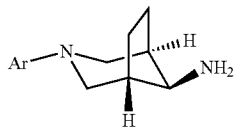

wherein Ar, $R^1$, n and m are as defined herein,
to form said compound of formula (I), and if desired, converting the compounds obtained into a pharmaceutically acceptable salt thereof.

A further object of the present invention is a compound of formula (I) as described herein, when manufactured according to the process as described above.

A further object of the present invention is a compound of formula (I) as described herein for use as a therapeutically active substance.

A further object of the present invention is a pharmaceutical composition comprising a compound of formula (I) as described herein and a therapeutically inert carrier.

A further object of the present invention is a compound of formula (I) as described herein for use in the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome.

A further object of the present invention is the use of a compound of formula (I) as described herein for the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome.

A further object of the present invention is the use of a compound of formula (I) as described herein for the preparation of a medicament for the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome.

A further object of the present invention is a method for the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome, which method comprises administering an effective amount of a compound of formula (I) as described herein.

DETAILED DESCRIPTION OF THE INVENTION

The following definitions of the general terms used in the present description apply irrespectively of whether the terms in question appear alone or in combination with other groups.

The term "lower alkyl", alone or in combination with other groups, refers to saturated straight- or branched-chain alkyl group, with single or multiple branching, wherein the alkyl group in general comprises 1 to 7 carbon atoms ("$C_{1-7}$-alkyl"), for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular lower alkyl groups have 1 to 4 carbon atoms ("$C_{1-4}$-alkyl").

The term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like. The preferred group is $CF_3$.

The term "alkoxy", alone or in combination, denotes a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular "alkoxy" are methoxy and tert-butyloxy.

The term "lower alkoxy substituted by halogen" denotes a lower alkoxy group as defined above, wherein at least one hydrogen atom is replaced by halogen.

The terms "halogen" or "halo", alone or in combination, denotes fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein.

Particularly preferred pharmaceutically acceptable salts of compounds of formula (I) are the salts of hydrochloric acid, hydrobromic acid, sulfuric acid, phosphoric acid and methanesulfonic acid.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protective groups can be removed at the appropriate point. Exemplary protective groups are amino-protective groups, carboxy-protective groups or hydroxy-protective groups. Particular protective groups are the tert-butoxycarbonyl (Boc), benzyloxycarbonyl (Cbz), fluorenylmethoxycarbonyl (Fmoc) and benzyl (Bn). Further particular protective groups are the tert-butoxycarbonyl (Boc) and the fluorenylmethoxycarbonyl (Fmoc). More particular protective group is the tert-butoxycarbonyl (Boc). Exemplary protective groups and their application in organic synthesis are described, for example, in "Protective Groups in Organic Chemistry" by T. W. Greene and P. G. M. Wutts, 5th Ed., 2014, John Wiley & Sons, N.Y.

The terms "asymmetric carbon atom" and "asymmetric center" mean a carbon atom with four different substituents. According to the Cahn-Ingold-Prelog Convention, an asymmetric carbon atom can be of the "R" or "S" configuration.

The following abbreviations are used in the present text: Boc=tert-butyloxycarbonyl, CAS RN=chemical abstracts registration number, DCM=dichloromethane, DIPEA=N,N-diisopropylethylamine, EtOAc=ethyl acetate, EtOH=ethanol, FCS=fetal calf serum, h=hour(s), Hal=halogen, HPLC=high-performance liquid chromatography, IMDM=Iscove's modified Dulbecco's medium, MeCN=acetonitrile, MeOH=methanol, Me$_2$SO=dimethylsulfoxide (DMSO), min=minute(s), mL=milliliter, μL=microliter, MS=mass spectrum, NaOMe=sodium methoxide, Na$^t$BuO=sodium tert-butyloxide, nBuLi=n-butyllithium, NEt$_3$=triethylamine (TEA), NMP=N-methyl-2-pyrrolidone, OAc=Acetoxy, Pd$_2$(dba)$_3$=tris(dibenzylideneacetone)dipalladium(0), p-TsOH=p-toluenesulfonic acid, R=any group, RT=room temperature, sat. aq. sol.=saturated aqueous solution, tBuXPhos=2-di-tert-butylphosphino-2',4',6'-triisopropylbiphenyl, TEA=triethylamine, TFA=trifluroacetic acid, THF=tetrahydrofuran, THP=tetrahydropyran.

Compounds of the Invention

In a first aspect, the present invention provides a compound of formula (I)

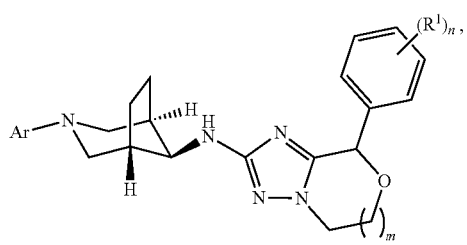

wherein
R$^1$ is halogen, lower alkyl, lower alkyl substituted by halogen, lower alkoxy, or lower alkoxy substituted by halogen,
and R$^1$ may be different if n=2 or 3;
m is 1 or 2;
n is 1, 2 or 3;
Ar is a six membered heteroaryl group, selected from

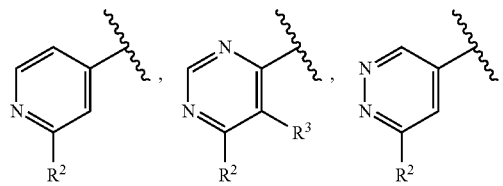

wherein
R$^2$ is hydrogen, halogen, lower alkyl, lower alkyl substituted by halogen, or lower alkoxy;
R$^3$ is hydrogen or halogen;
or a pharmaceutically acceptable salt thereof.

In one embodiment, there is provided a compound of formula (I) as described herein, wherein the compound of formula (I) is a compound of formula (Ia):

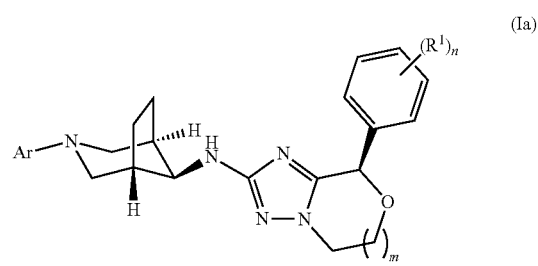

wherein R$^1$, m, n and Ar are as defined above.

In one embodiment, there is provided a compound of formula (I) as described herein, wherein the compound of formula (I) is a compound of formula (Ib):

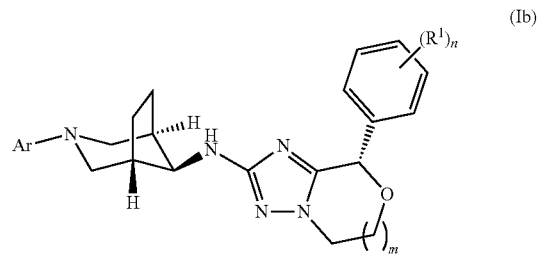

wherein R$^1$, m, n and Ar are as defined above.

In one embodiment, R$^1$ is halogen.

In a preferred embodiment, R$^1$ is fluorine or chlorine.

In one embodiment, n is 2 or 3.

In a preferred embodiment, there is provided a compound of formula (I) as described herein, wherein Ar is a six membered heteroaryl group, selected from

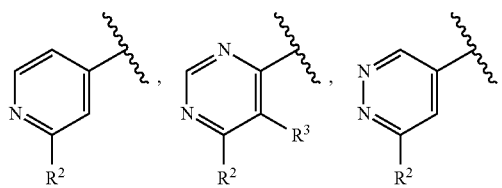

wherein
R² is lower alkyl or lower alkoxy;
R³ is hydrogen.

In a further preferred embodiment, there is provided a compound of formula (I) as described herein, wherein Ar is a six membered heteroaryl group, selected from

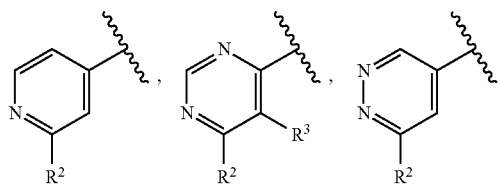

wherein
R² is methyl or methoxy;
R³ is hydrogen.

In a further preferred embodiment, there is provided a compound of formula (I) as described herein,
wherein:
R¹ is halogen;
m is 1 or 2;
n is 2 or 3;
Ar is a six membered heteroaryl group, selected from

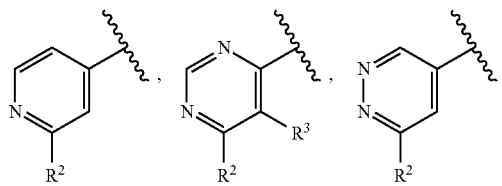

wherein
R² is lower alkyl or lower alkoxy;
R³ is hydrogen.

In a further preferred embodiment, there is provided a compound of formula (I) as described herein,
wherein:
R¹ is fluorine or chlorine,
m is 1 or 2;
n is 2 or 3;
Ar is a six membered heteroaryl group, selected from

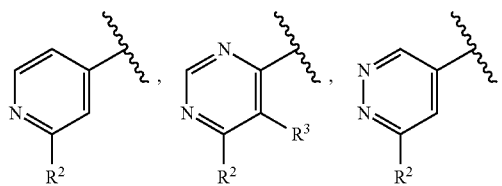

wherein
R² is methyl or methoxy;
R³ is hydrogen.

The compound of formula (I) may contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

In a further preferred embodiment, there is provided a compound of formula (I) as described herein, selected from
(9R)-9-(2,3-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,3-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9R)-9-(2,4-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,4-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9R)-9-(2,3-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,3-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(3,5-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3,5-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(2,4-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,4-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(3,5-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3,5-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9R)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9R)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;
(9R)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9R)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;

(9S)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;

(8R)-8-(3-chloro-5-fluoro-phenyl)-N-[(1R,5S)-3-(6-methoxypyridazin-4-yl)-3-azabicyclo[3.2.1]octan-8-yl]-6,8-dihydro-5H-[1,2,4]triazolo[5,1-c][1,4]oxazin-2-amine;

(8S)-8-(3-chloro-5-fluoro-phenyl)-N-[(1R,5S)-3-(6-methoxypyridazin-4-yl)-3-azabicyclo[3.2.1]octan-8-yl]-6,8-dihydro-5H-[1,2,4]triazolo[5,1-c][1,4]oxazin-2-amine;

(8R)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8S)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8R)-8-(3-chloro-5-fluoro-phenyl)-N-[(1R,5S)-3-(6-methylpyrimidin-4-yl)-3-azabicyclo[3.2.1]octan-8-yl]-6,8-dihydro-5H-[1,2,4]triazolo[5,1-c][1,4]oxazin-2-amine;

(8S)-8-(3-chloro-5-fluoro-phenyl)-N-[(1R,5S)-3-(6-methylpyrimidin-4-yl)-3-azabicyclo[3.2.1]octan-8-yl]-6,8-dihydro-5H-[1,2,4]triazolo[5,1-c][1,4]oxazin-2-amine;

(8R)—N-[(1R,5S)-3-(6-methoxypyridazin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8S)—N-[(1R,5S)-3-(6-methoxypyridazin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8R)-8-(3-chloro-5-fluoro-phenyl)-N-[(1R,5S)-3-(2-methoxy-4-pyridyl)-3-azabicyclo[3.2.1]octan-8-yl]-6,8-dihydro-5H-[1,2,4]triazolo[5,1-c][1,4]oxazin-2-amine;

(8S)-8-(3-chloro-5-fluoro-phenyl)-N-[(1R,5S)-3-(2-methoxy-4-pyridyl)-3-azabicyclo[3.2.1]octan-8-yl]-6,8-dihydro-5H-[1,2,4]triazolo[5,1-c][1,4]oxazin-2-amine;

(8R)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8S)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(9R)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;

(9S)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;

(9R)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;

(9S)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;

(9R)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9S)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9R)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9S)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

or a pharmaceutically acceptable salt thereof.

In a more preferred embodiment, there is provided a compound of formula (I) as described herein, selected from (9R)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9S)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9R)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;

(9S)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;

(9R)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9S)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9R)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;

(9S)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;

(8R)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8S)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8R)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8S)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(9R)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;

(9S)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;

(9R)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;

(9S)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;

(9R)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9S)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

(9R)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
or a pharmaceutically acceptable salt thereof.

Processes of Manufacturing

Processes for the manufacture of compounds of formula (I) as described herein are also an object of the present invention.

The preparation of compounds of formula (I) as described herein may be carried out in sequential or convergent synthetic routes. Syntheses of the invention are shown in the following general schemes. The skills required for carrying out the reactions and purifications of the resulting products are known to those skilled in the art. The substituents and indices used in the following description of the processes have the significance given herein before unless indicated to the contrary.

If one of the starting materials, intermediates or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

If starting materials or intermediates contain stereogenic centers, compounds of formula (I) can be obtained as mixtures of diastereomers or enantiomers, which can be separated by methods well known in the art e.g., chiral HPLC, chiral SFC or chiral crystallization. Racemic compounds can, for example, be separated into their antipodes via diastereomeric salts by crystallization with optically pure acids or by separation of the antipodes by specific chromatographic methods using either a chiral adsorbent or a chiral eluent. It is equally possible to separate starting materials and intermediates containing stereogenic centers to afford diastereomerically/enantiomerically enriched starting materials and intermediates. Using such diastereomerically/enantiomerically enriched starting materials and intermediates in the synthesis of compounds of formula (I) will typically lead to the respective diastereomerically/enantiomerically enriched compounds of formula (I).

A person skilled in the art will acknowledge that the sequence of reactions may be varied depending on reactivity and nature of the intermediates.

In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 2nd Edition*, Richard C. Larock. John Wiley & Sons, New York, NY. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

If starting materials or intermediates are not commercially available or their synthesis not described in literature, they can be prepared in analogy to existing procedures for close analogues or as outlined in the experimental section.

In one embodiment, compounds of formula (I) as described herein may be prepared by a process comprising reacting a compound 5

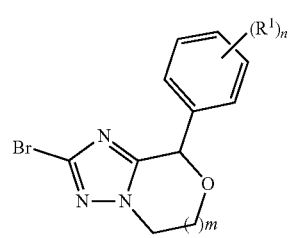

5 with an amine 6

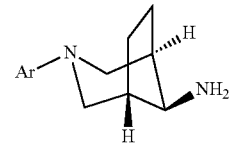

6 wherein Ar, $R^1$, n and m are as defined herein
to form said compound of formula (I), and if desired, converting said compound obtained into a pharmaceutically acceptable salt thereof.

In one embodiment, the process according to the invention can be carried out in the presence of a catalyst, e.g palladium, optionally in the presence of a ligand, e.g 2-di-tert-butylphosphino-2',4',6'-triisopropylbiphenyl.

In a further embodiment, the process according to the invention can further comprise a step of performing a chiral separation to obtain compounds of formulas (Ia) and (Ib).

In one embodiment, compounds of formula (I) wherein $R^1$, n, m and Ar are as described herein and their intermediates may be prepared in analogy to literature procedures and/or depicted for example in schemes 1 and 2 respectively.

Scheme 1

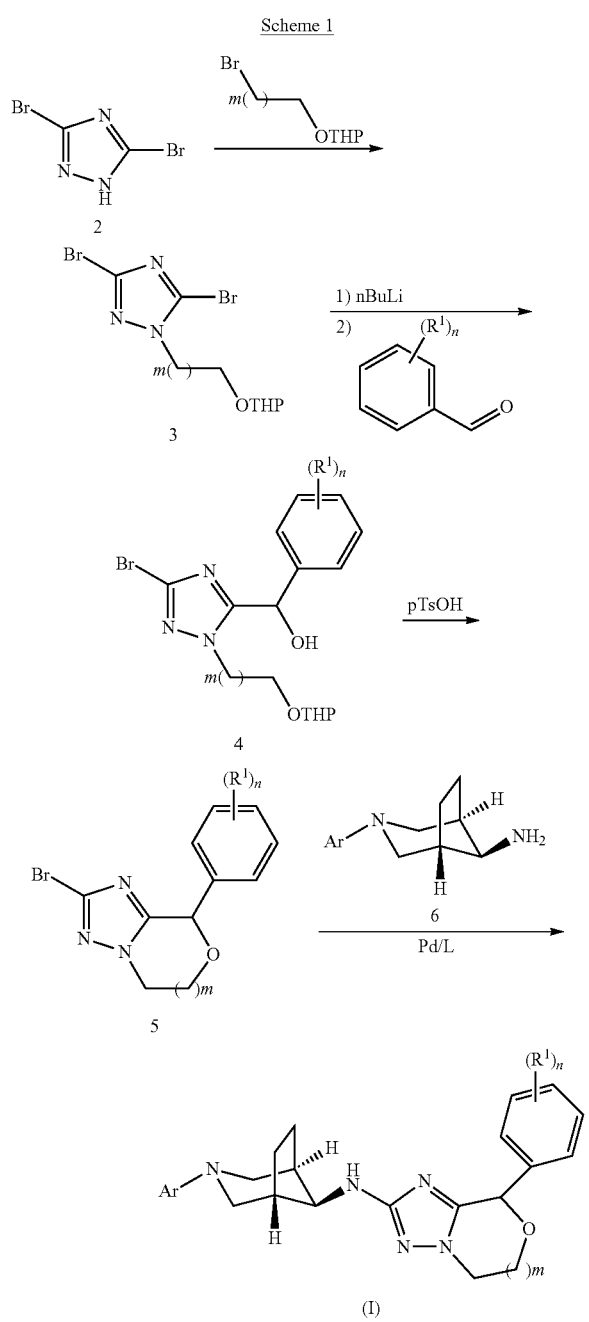

The preparation of compounds of formula (I) may start with the alkylation of 3,5-dibromo-1H-1,2,4-triazole 2 with as electrophile either 2-(2-bromoethoxy)tetrahydropyran (if m equal 1) or 2-(3-bromopropoxy)tetrahydropyran (if m equal 2) to yield compound 3. A regioselective halo lithiation with nBuLi followed by the addition of an optionally substituted benzaldehyde derivative affords primary alcohol 4. After deprotection of the primary alcohol 4 with pTsOH, an intramolecular etherification may be performed using pTsOH at high temperature to yield intermediate 5. Finally, a Buchwald type coupling with amine 6 in the presence of palladium and a ligand affords the compounds of formula (I). A preparative chiral HPLC may be performed to separate the enantiomers.

Intermediates 6 may be synthesized as depicted for example in scheme 2 and/or in analogy to methods described in literature.

Scheme 2

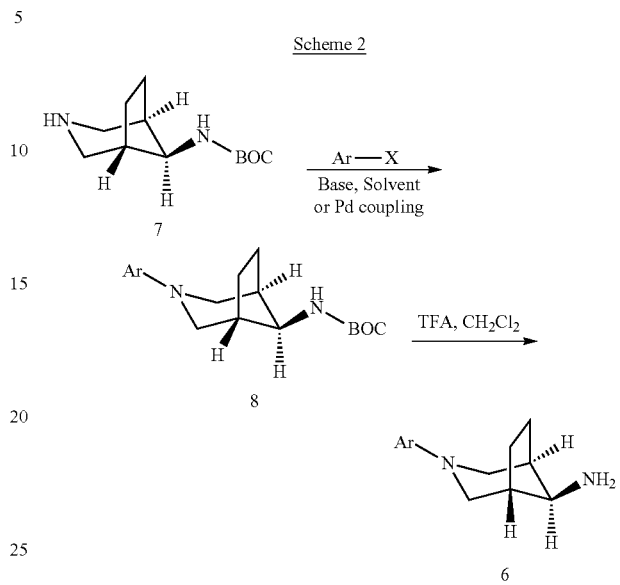

The coupling of tert-butyl N-[(1S,5R,8S)-3-azabicyclo[3.2.1]octan-8-yl]carbamate 7 (CAS 847862-26-4) with heterocyclic halides of general formula Ar—X can be accomplished under thermal conditions in a solvent such as ethanol or NMP in the presence of a base such as $Et_3N$ or by using displacement reactions under catalytic conditions (like e.g. palladium(0) or copper(II) catalysis) to provide intermediates 8. Deprotection with acid, e.g. trifluoroacetic acid affords amine 6. The heterocyclic halides are either commercially available or well known in the literature so they can be prepared by methods known in the art.

In one aspect, the present invention provides a compound of formula (I) as described herein, when manufactured according to any one of the processes described herein.

Pharmaceutical Composition and Administration

Another object of the present invention is a pharmaceutical composition comprising a compound of formula (I) as described herein and a therapeutically inert carrier.

The compounds of formula I and their pharmaceutically acceptable salts can be used as medicaments, in the form of pharmaceutical preparations. The pharmaceutical preparations can be administered internally, such as orally (e.g. in the form of tablets, coated tablets, drages, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions). The administration can also be effected topically, e.g. transdermal administration, or in form of eye drops or ear drops.

The compounds of formula (I) and their pharmaceutically acceptable salts can be processed with pharmaceutically inert, inorganic or organic carriers for the production of pharmaceutical preparations, such as tablets, coated tablets, dragées, hard gelatin capsules, injection solutions or topical formulations. Lactose, corn starch or derivatives thereof, talc, stearic acids or salts thereof, and the like can be used, for example, as such carriers for tablets, coated tablets, dragées and hard gelatin capsules.

Suitable carriers for soft gelatin capsules are, for example, vegetable oils, waxes, fats, semi-solid substances and liquid polyols and the like. Depending on the nature of the active substance no carriers are, however, usually required in the case of soft gelatin capsules.

Suitable carriers for the production of solutions and syrups are, for example, water, alcohols, polyols, saccharose, glucose, invert sugar, vegetable oil, etc.

Suitable carriers for injection solutions are, for example, water, alcohols, polyols, glycerol, vegetable oils, etc.

Suitable carriers for suppositories are, for example, natural or hardened oils, waxes, fats, semi-liquid or liquid polyols, etc.

Suitable carriers for topical ocular formulations are, for example, cyclodextrins, mannitol or many other carriers and excipients known in the art.

Moreover, the pharmaceutical preparations can contain preservatives, solubilizers, viscosity increasing substances, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula (I) or a pharmaceutically acceptable salt thereof and a therapeutically inert carrier are also an object of the present invention, as is a process for their production, which comprises bringing one or more compounds of formula (I) and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In general, in the case of oral administration a daily dosage of about 0.1 mg to 20 mg per kg body weight, preferably 0.5 mg to 4 mg per kg body weight (e.g. about 300 mg per person), divided into preferably 1-3 individual doses, which can consist, for example, of the same amounts, should be appropriate. In the case of topical administration, the formulation can contain 0.001% to 15% by weight of medicament and the required dose, which can be between 0.1 and 25 mg, and can be administered either by single dose per day or per week, or by multiple doses (2 to 4) per day, or by multiple doses per week. It will, however, be clear that the upper or lower limit given herein can be exceeded when this is shown to be indicated.

Preparation of Pharmaceutical Compositions Comprising Compounds of the Invention

| Tablet Formulation (Wet Granulation) | | | | |
| --- | --- | --- | --- | --- |
| | mg/tablet | | | |
| Ingredient | 5 | 25 | 100 | 500 |
| 1) Compound of formula (I) | 5 | 25 | 100 | 500 |
| 2) Lactose Anhydrous DTG | 125 | 105 | 30 | 150 |
| 3) Sta-Rx 1500 | 6 | 6 | 6 | 30 |
| 4) Microcrystalline Cellulose | 30 | 30 | 30 | 150 |
| 5) Magnesium Stearate | 1 | 1 | 1 | 1 |
| Total | 167 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

| Capsule Formulation | | | | |
| --- | --- | --- | --- | --- |
| | mg/capsule | | | |
| Ingredient | 5 | 25 | 100 | 500 |
| 1) Compound of formula (I) | 5 | 25 | 100 | 500 |
| 2) Hydrous Lactose | 159 | 123 | 148 | — |
| 3) Corn Starch | 25 | 35 | 40 | 70 |
| 4) Talc | 10 | 15 | 10 | 25 |
| 5) Magnesium Stearate | 1 | 2 | 2 | 5 |
| Total | 200 | 200 | 300 | 600 |

Manufacturing Procedure:

1. Mix ingredients 1, 2 and 3 in a suitable mixer for 30 minutes.
2. Add ingredients 4 and 5 and mix for 3 minutes.
3. Fill into a suitable capsule.

Indications

Also an object of the present invention is a compound of formula (I) as described herein for use as a therapeutically active substance.

As described above, compounds of formula (I) and their pharmaceutically acceptable salts are useful as gamma-secretase modulators.

In one aspect, the present invention provides compounds of formula (I) as described herein for use in the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome.

In one embodiment, the present invention provides compounds of formula (I) as described herein for use in the therapeutic and/or prophylactic treatment of Alzheimer's disease.

In a further aspect, the present invention provides the use of compounds of formula (I) as described herein for the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome.

In one embodiment, the present invention provides the use of compounds of formula (I) as described herein for the therapeutic and/or prophylactic treatment of Alzheimer's disease.

In a further aspect, the present invention provides the use of compounds of formula (I) as described herein for the preparation of a medicament for the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome.

In one embodiment, the present invention provides the use of compounds of formula (I) for the preparation of a medicament for the therapeutic and/or prophylactic treatment of Alzheimer's disease.

In a further aspect, the present invention provides a method for the therapeutic and/or prophylactic treatment of Alzheimer's disease, cerebral amyloid angiopathy, hereditary cerebral hemorrhage with amyloidosis-Dutch type (HCHWA-D), multi-infarct dementia, dementia pugilistica, or Down syndrome, which method comprises administering an effective amount of a compound of formula (I) as described herein.

In one embodiment, the present invention provides a method for the therapeutic and/or prophylactic treatment of Alzheimer's disease which method comprises administering an effective amount of a compound of formula (I) as described herein.

EXAMPLES

The invention will be more fully understood by reference to the following examples. The claims should not, however, be construed as limited to the scope of the examples.

1) Preparative Examples 1.1) General

Analytical method: HPLC (method LCMS_fastgradient)

Column: Agilent Zorbax Eclipse Plus C18, Rapid Resolution HT, 2.1×30 mm, 1.8 μm, Part. no. 959731-902

Solvent A: Water 0.01% Formic Acid; Solvent B: acetonitrile (MeCN)

Gradients:

| Time [min] | Flow Rate [ml/min] | % A | % B |
| --- | --- | --- | --- |
| Initial | 0.8 | 97 | 3 |
| 0.2 | 1.0 | 97 | 3 |
| 1.7 | 1.0 | 3 | 97 |
| 2.0 | 1.0 | 3 | 97 |
| 2.1 | 1.0 | 97 | 3 |

1.2) Preparation of Intermediates 1.2.1) Intermediates of Type 5, with m=1

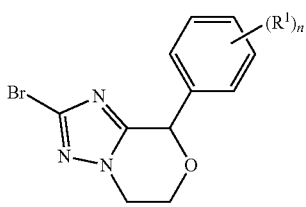

Intermediate 5-1

2-bromo-8-(2,3,4-trifluorophenyl)-6,8-dihydro-5H-[1,2,4]triazolo[5,1-c][1,4]oxazine

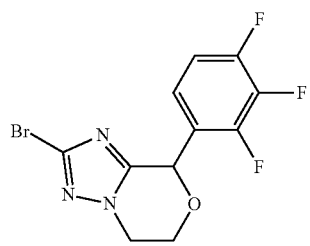 [SMILES: Fc1ccc(C2OCCn3nc(Br)nc32)c(F)c1F]

Step 1: 2-(2-bromoethoxy)tetrahydro-2H-pyran (10.0 g, 7.23 ml, 47.8 mmol, Eq: 1.00) and DIPEA (6.18 g, 8.35 ml, 47.8 mmol, Eq: 1.00) were added to a suspension of 3,5-dibromo-1H-1,2,4-triazole (10.9 g, 47.8 mmol, Eq: 1.00) in MeCN (90 ml) and then stirred at 90° C. for 20 hr. The reaction mixture was cooled to RT, and concentrated in vacuo. The residue was purified by flash column chromatography over silica gel (eluent: EtOAc/heptane from 10/90 to 60/40) to yield 3,5-dibromo-1-(2-tetrahydropyran-2-yloxyethyl)-1,2,4-triazole (12.08 g, 33.7 mmol, 70% yield) as a light yellow oil. MS (ES+) m/z: 356.0 [(M+H)⁺].

Step 2: n-BuLi (1.6 M in hexane, 7.04 ml, 11.3 mmol, Eq: 1.00) was added to a solution of 3,5-dibromo-1-(2-((tetrahydro-2H-pyran-2-yl)oxy)ethyl)-1H-1,2,4-triazole (4.00 g, 11.3 mmol, Eq: 1.00) in THF (100 ml) at −78° C. The reaction was stirred for 20 min at −78° C., after which a solution of 2,3,4-trifluorobenzaldehyde (1.80 g, 11.3 mmol, Eq: 1.00) in THF (30.0 ml) was added. The solution was stirred at −78° C. for an additional 2 hours. The reaction temperature was gradually increased to RT and quenched with the addition of a sat. aq. sol. of NH₄Cl (5.00 ml). The reaction was diluted with EtOAc (150 ml) and washed with brine (2×50 ml). The organic phase was separated and dried over Na₂SO₄, filtered off and concentrated in vacuo. The residue was purified by flash column chromatography over silica gel (eluent: EtOAc/heptane from 10/90 to 50/50) to yield [5-bromo-2-(2-tetrahydropyran-2-yloxyethyl)-1,2,4-triazol-3-yl]-(2,3,4-trifluorophenyl)methanol (4.50 g, 10.2 mmol, 91% yield) as a pale yellow oil. MS (ES+) m/z: 436.1 [(M+H)⁺].

Step 3: p-Toluenesulfonic acid monohydrate (402 mg, 2.11 mmol, Eq: 0.20) was added to a solution of [5-bromo-2-(2-tetrahydropyran-2-yloxyethyl)-1,2,4-triazol-3-yl]-(2,3,4-trifluorophenyl)methanol (4.61 g, 10.6 mmol, Eq: 1.00) in MeOH (143 ml). The reaction was stirred for 2 hr. at RT and then concentrated in vacuo. The residue was dissolved in DCM (95.0 nil), washed with a sat. aq. sol. of NaHCO₃ (50.0 ml), and the organic phase separated and dried over Na₂SO₄, concentrated and dried in vacuo to yield 2-[3-bromo-5-[hydroxy-(2,3,4-trifluorophenyl)methyl]-1,2,4-triazol-1-yl]ethanol (3.42 g, 8.45 mmol, 80% yield) as a light yellow oil, which was further used without purification. MS (ES+) m/z: 354.0 [(M+H)⁺].

Step 4: p-Toluenesulfonic acid monohydrate (1.85 g, 9.71 mmol, Eq: 1.00) was added to a solution of crude 2-(3-bromo-5-(hydroxy(2,3,4-trifluorophenyl)methyl)-1H-1,2,4-triazol-1-yl)ethan-1-ol (3.42 g, 9.71 mmol, Eq: 1.00) in xylene (140 ml). The solution was refluxed at 170° C. for 16 hours using a Dean-Stark apparatus to remove water. The reaction mixture was then left to cool to RT. The residue was diluted with EtOAc (100 ml) and washed with an aq. sol. of Na$_2$CO$_3$ (50.0 ml). The organic phase was separated and dried over Na$_2$SO$_4$ and a purification by flash column chromatography over silica gel (eluent: EtOAc/heptane from 0/100 to 60/40) yielded 2-bromo-8-(2,3,4-trifluorophenyl)-6,8-dihydro-5H-[1,2,4]triazolo[5,1-c][1,4]oxazine (1.37 g, 4.06 mmol, 42% yield) as an off white solid. MS (ES+) m/z: 334.0 [(M+H)$^+$].

Intermediate 5-2

2-bromo-8-(3-chloro-5-fluoro-phenyl)-6,8-dihydro-5H-[1,2,4]triazolo[5,1-c][1,41]oxazine

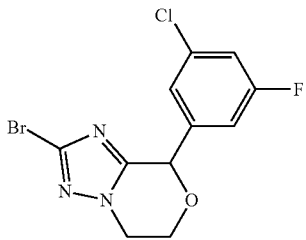 [SMILES: Fc1cc(Cl)cc(C2OCCn3nc(Br)nc32)c1]

In analogy to the preparation of the intermediate 5-1; but using in the second step the 3-chloro-5-fluoro-benzaldehyde, the title product was obtained as a white solid. MS (ES+) m/z: 334.0 [(M+H)$^+$].

1.2.2) Intermediates of Type 5, with m=2

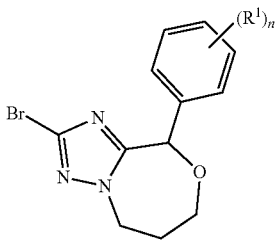

Intermediate 5-3

2-bromo-9-(3-chloro-5-fluoro-phenyl)-5,6,7,9-tetrahydro-[1,2,4]triazolo[5,1-c][1,4]oxazepine

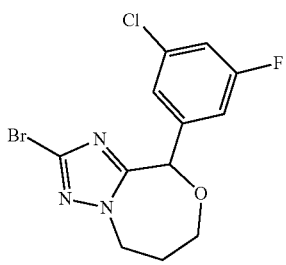 [SMILES: Fc1cc(Cl)cc(C2OCCCn3nc(Br)nc32)c1]

Step 1: 2-(3-bromopropoxy)tetrahydro-2H-pyran (5.60 g, 4.25 ml, 25.1 mmol, Eq: 1.00) and DIPEA (3.24 g, 4.38 ml, 25.1 mmol, Eq: 1.00) were added to a suspension of 3,5-dibromo-1H-1,2,4-triazole (5.69 g, 25.1 mmol, Eq: 1.00) in MeCN (50.0 ml). The reaction was stirred at 90° C. for 3 hr, cooled down to RT and concentrated in vacuo. The residue was purified by flash column chromatography over silica gel (eluent: EtOAc/heptane from 20/80 to 60/40) to yield 3,5-dibromo-1-(3-tetrahydropyran-2-yloxypropyl)-1,2,4-triazole (7.50 g, 19.7 mmol, 79% yield) as light yellow oil.

Step 2: n-BuLi (1.6M in hexane, 4.04 g, 5.94 ml, 9.51 mmol, Eq: 1.00) was added to a solution of 3,5-dibromo-1-(3-tetrahydropyran-2-yloxypropyl)-1,2,4-triazole (3.50 g, 9.48 mmol, Eq: 1.00) in THF (110 ml) at −78° C. The reaction mixture was stirred for 20 min. at −78° C., after which a solution of 3-chloro-5-fluorobenzaldehyde (1.50 g, 9.48 mmol, Eq: 1.00) in THF (25.0 ml) was added and stirring continued at −78° C. for 1 hr, then the temperature was gradually increased to RT. The reaction was quenched with the addition of a sat. aq. sol. of NH$_4$Cl (5.00 ml) and diluted with EtOAc (100 ml), washed with brine (2×100 ml), before the organic phase was separated and dried over Na$_2$SO$_4$, and concentrated under vacuo. The residue was purified by flash column chromatography over silica gel (eluent: EtOAc/heptane from 20/80 to 75/25) to yield [5-bromo-2-(3-tetrahydropyran-2-yloxypropyl)-1,2,4-triazol-3-yl]-(3-chloro-5-fluorophenyl)methanol (1.94 g, 4.28 mmol, 45% yield) as a pale yellow oil. MS (ES+) m/z: 450.1 [(M+H)$^+$].

Step 3: p-Toluenesulfonic acid monohydrate (164 mg, 865 µmol, Eq: 0.20) was added to a solution of [5-bromo-2-(3-tetrahydropyran-2-yloxypropyl)-1,2,4-triazol-3-yl]-(3-chloro-5-fluorophenyl)methanol (1.94 g, 4.32 mmol, Eq: 1.00) in MeOH (60.0 ml). The reaction was stirred for 2 h at RT and then concentrated in vacuo. The residue was then dissolved in DCM (40.0 ml), washed with a sat. aq. sol. of NaHCO$_3$ (50 ml), and the organic phase was dried over Na$_2$SO$_4$ and concentrated in vacuo to yield 3-[3-bromo-5-[(3-chloro-5-fluoro-phenyl)-hydroxy-methyl]-1,2,4-triazol-1-yl]propan-1-ol (1.48 g, 3.73 mmol, 86% yield) as a light yellow viscous oil, which was further used without purification. MS (ES+) m/z: 366.0 [(M+H)$^+$].

Step 4: p-Toluenesulfonic acid monohydrate (772 mg, 4.06 mmol, Eq: 1.00) was added to a solution of crude 3-[3-bromo-5-[(3-chloro-5-fluoro-phenyl)-hydroxy-methyl]-1,2,4-triazol-1-yl]propan-1-ol (1.48 g, 4.06 mmol, Eq: 1.00) in xylene (60.0 ml). The solution was refluxed at 170° C. for 17 h using a Dean-Stark apparatus to remove water. The reaction mixture was then cooled down to RT, diluted with EtOAc (100 ml) and washed with an aq. sol. of Na$_2$CO$_3$ (50 ml). The organic phase was separated and dried over Na$_2$SO$_4$ and then concentrated in vacuo. The residue was purified by flash column chromatography over silica gel (eluent: EtOAc/heptane from 20/80 to 80/20) to yield 2-bromo-9-(3-chloro-5-fluoro-phenyl)-5,6,7,9-tetrahydro-[1,2,4]triazolo[5,1-c][1,4]oxazepine (685 mg, 1.96 mmol, 48% yield) as a light brown solid. MS (ES+) m/z: 350.0 [(M+H)$^+$].

Intermediate 5-4

2-bromo-9-(2,3-difluorophenyl)-5,6,7,9-tetrahydro-[1,2,4]triazolo[5,1-c][1,4]oxazepine

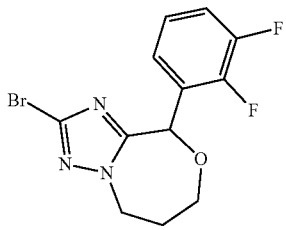 [SMILES: Fc1cccc(C2OCCCn3nc(Br)nc32)c1F]

In analogy to the preparation of the intermediate 5-3, but using in the second step 2,3-difluorobenzaldehyde, the title compound was prepared as a white solid. MS (ES+) m/z: 330.0/332.0 [(M+H)+].

Intermediate 5-5:

2-bromo-9-(2,4-difluorophenyl)-5,6,7,9-tetrahydro-[1,2,4]triazolo[5,1-c][1,4]oxazepine

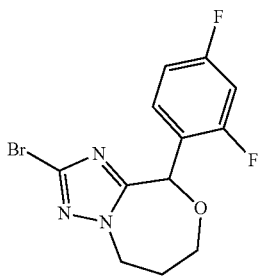 [SMILES: Fc1ccc(C2OCCCn3nc(Br)nc32)c(F)c1]

In analogy to the preparation of the intermediate 5-3, but using in the second step 2,4-difluorobenzaldehyde, the title compound was prepared as a white solid. MS (ES+) m/z: 330.0 [(M+H)+].

Intermediate 5-6

2-bromo-9-(3,5-difluorophenyl)-5,6,7,9-tetrahydro-[1,2,4]triazolo[5,1-c][1,4]oxazepine

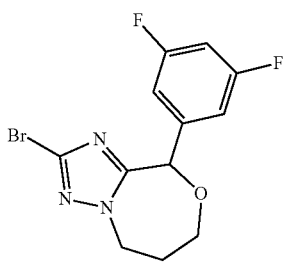 [SMILES: Fc1cc(F)cc(C2OCCCn3nc(Br)nc32)c1]

In analogy to the preparation of the intermediate 5-3, but using in the second step 3,5-difluorobenzaldehyde, the title compound was prepared as a white solid. MS (ES+) m/z: 330.1 [(M+H)+].

Intermediate 5-7

2-bromo-9-(2,3,4-trifluorophenyl)-5,6,7,9-tetrahydro-[1,2,4]triazolo[5,1-c][1,4]oxazepine

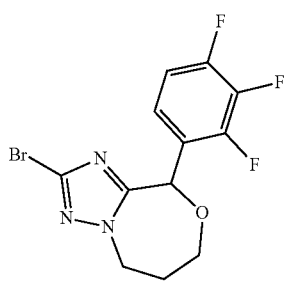 [SMILES: Fc1ccc(C2OCCCn3nc(Br)nc32)c(F)c1F]

In analogy to the preparation of the intermediate 5-3, but using in the second step 2,3,4-trifluorobenzaldehyde, the title compound was prepared as a white solid. MS (ES+) m/z: 350.1 [(M+H)+].

1.2.3) Intermediates of type 6

Intermediate 6-1

(1R,5S,8S)-3-(6-methylpyrimidin-4-yl)-3-azabicyclo[3.2.1]octan-8-amine

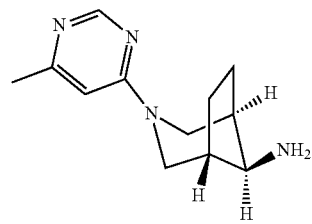 [SMILES: Cc1cc(N2C[C@H]3CC[C@@H](C2)[C@@H]3N)ncn1]

Step 1: In a sealed tube tert-butyl N-[(1R,5S,8S)-3-azabicyclo[3.2.1]octan-8-yl]carbamate (500 mg, 2.21 mmol) was dissolved in EtOH (10 mL) and 4-chloro-6-methylpyrimidine (869 mg, 6.63 mmol) was added followed by triethylamine (894 mg, 1.23 mL, 8.84 mmol). The reaction mixture was stirred at 130° C. overnight. The crude reaction mixture was concentrated in vacuo. The residue was diluted with 20 mL of CH₂Cl₂ and 20 mL of water. The organic phase was extracted with CH₂Cl₂ (3×20 mL), dried over MgSO₄ and concentrated in vacuo. The crude material was purified by flash chromatography (0% to 100% EtOAc in heptane) to afford tert-butyl N-[(1R,5S,8S)-3-(6-methylpyrimidin-4-yl)-3-azabicyclo [3.2.1]octan-8-yl]carbamate as a yellow solid (496 mg, 71% yield). MS (ES+) m/z: 319.2 [(M+H)+].

Step 2: To a light yellow solution of tert-butyl N-[(1R,5S,8S)-3-(6-methylpyrimidin-4-yl)-3-azabicyclo[3.2.1]octan-8-yl]carbamate (260 mg, 817 μmol) in CH₂Cl₂ (8 mL) was added TFA (931 mg, 629 μl, 8.17 mmol). The reaction mixture was stirred at room temperature over night and concentrated in vacuum. The crude material was purified by Ion-exchange column (Si—SCX-2, 10 g, washed with MeOH and liberated with MeOH (NH₃ 2M)) to afford (1R,5S,8S)-3-(6-methylpyrimidin-4-yl)-3-azabicyclo[3.2.1]octan-8-amine 6-1 (195 mg, 804 µmol, 98.5% yield) that was used in the next step without further purification. MS (ES+) m/z: 219.2 [(M+H)⁺].

Intermediate 6-2

(1R,5S,8S)-3-(2-methoxy-4-pyridyl)-3-azabicyclo[3.2.1]octan-8-amine

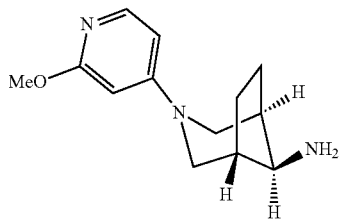 [SMILES: COc1cc(N2C[C@H]3CC[C@@H](C2)[C@@H]3N)ccn1]

Step 1: In analogy to the preparation of the intermediate 6-1 (step 1) from tert-butyl N-[(1R,5S,8S)-3-azabicyclo[3.2.1]octan-8-yl]carbamate (2.00 g, 8.84 mmol) and 4-fluoro-2-methoxypyridine (1.12 g, 8.84 mmol) in a sealed tube at 140° C. using NMP as solvent in the presence of DIPEA (2.28 g, 3.09 mL, 17.70 mmol), tert-butyl N-[(1R,5S,8S)-3-(2-methoxy-4-pyridyl)-3-azabicyclo[3.2.1]octan-8-yl]carbamate (1.42 g, 48%) was obtained as a white solid. MS (ES+) m/z: 334.3 [(M+H)⁺].

Step 2: In analogy to the preparation of intermediate 6-1 (step 2) from tert-butyl N-[(1R,5S,8S)-3-(2-methoxy-4-pyridyl)-3-azabicyclo[3.2.1]octan-8-yl]carbamate (1.42 g, 4.26 mmol) in CH₂Cl₂ in the presence of TFA (7.38 g, 5.0 mL, 15.2 mmol), (1R,5S,8S)-3-(2-methoxy-4-pyridyl)-3-azabicyclo[3.2.1]octan-8-amine 6-2 (0.89 g, 89%) was obtained as a white solid and used directly in the next step without further purification. MS (ES+) m/z: 234.2 [(M+H)⁺].

Intermediate 6-3

(1R,5S,8S)-3-(6-methoxypyridazin-4-yl)-3-azabicyclo[3.2.1]octan-8-amine

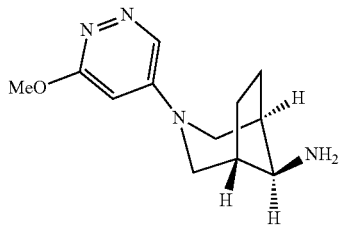 [SMILES: COc1cc(N2C[C@H]3CC[C@@H](C2)[C@@H]3N)cnn1]

Step 1: In analogy to the preparation of the intermediate 6-1 (step 1) from tert-butyl N-[(1R,5S,8S)-3-azabicyclo[3.2.1]octan-8-yl]carbamate (2.00 g, 8.84 mmol) and 3,5-dichloropyridazine (2.0 g, 13.4 mmol) in a sealed tube at 90° C. using EtOH as solvent in the presence of Et₃N (3.63 g, 5.0 mL, 35.9 mmol), tert-butyl N-[(1R,5S,8S)-3-(6-chloropyridazin-4-yl)-3-azabicyclo[3.2.1]octan-8-yl]carbamate (1.71 g, 54%) was obtained as a white solid. MS (ES+) m/z: 339.2 [(M+H)⁺].

Step 2: To a solution of tert-butyl N-[(1R,5S,8S)-3-(6-chloropyridazin-4-yl)-3-azabicyclo[3.2.1]octan-8-yl]carbamate (963 mg, 2.70 mmol) in MeOH (22 mL) in a sealed tube was added a methanol solution of NaOMe (25%, 1.9 mL, 8.3 mmol). The reaction mixture was heated at 85° C. overnight. The reaction mixture was adsorbed on Isolute HM-N and a column chromatography gave tert-butyl N-[(1R,5S,8S)-3-(6-methoxypyridazin-4-yl)-3-azabicyclo[3.2.1]octan-8-yl]carbamate (362 mg, 38%) as a white solid. MS (ES+) m/z: 335.2 [(M+H)⁺].

Step 3: In analogy to the preparation of intermediate 6-1 (step 2) from tert-butyl N-[(1R,5S,8S)-3-(6-methoxypyridazin-4-yl)-3-azabicyclo[3.2.1]octan-8-yl]carbamate (0.93 g, 2.72 mmol) in CH₂Cl₂ in the presence of TFA (1.12 g, 0.76 mL, 9.86 mmol), (1R,5S,8S)-3-(6-methoxypyridazin-4-yl)-3-azabicyclo[3.2.1]octan-8-amine 6-3 (225 mg, 96%) was obtained as a white solid and used directly in the next step without further purification. MS (ES+) m/z: 235.2 [(M+H)⁺].

Intermediate 6-4

(1R,5S,8S)-3-(6-methylpyridazin-4-yl)-3-azabicyclo[3.2.1]octan-8-amine

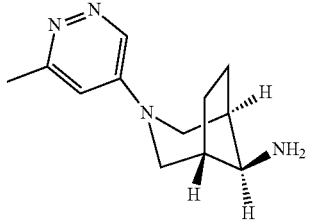 [SMILES: Cc1cc(N2C[C@H]3CC[C@@H](C2)[C@@H]3N)cnn1]

In a similar manner as for the intermediates 6-1 and 6-2, the title compound 6-4 was produced starting from tert-butyl N-[(1R,5S,8S)-3-azabicyclo[3.2.1]octan-8-yl]carbamate and 5-chloro-3-methyl-pyridazine as a white solid. MS (ES+) m/z: 219.3 [(M+H)⁺].

1.3) General Procedure 1: Buchwald Coupling Reaction

In a sealed tube, to a solution of an intermediate 5 (1 mmol) in 2-Me-THF (10 ml) was added 1.1 equivalent of an intermediate 6. The reaction mixture was degased and NaOtBu (1.5 eq.) was added at RT and the stirring continued for 15 minutes before tBu-Xphos (0.06 eq.) and Pd₂(dba)₃ (0.03 eq.) were added. The reaction mixture was heated at 60-80° C. until completion of the reaction (usually between 2 and 8 hours) and concentrated in vacuo. A purification was done either by flash column chromatography or reverse phase preparative HPLC to afford the desired product of formula 1.

Examples 1 and 2

(9R)-9-(2,3-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine and (9S)-9-(2,3-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine

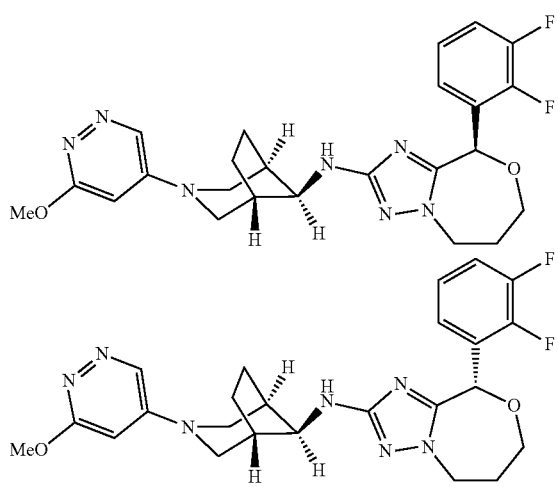

A Buchwald type coupling using the general procedure 1, between 2-bromo-9-(2,3-difluorophenyl)-5,6,7,9-tetrahydro-[1,2,4]triazolo[5,1-c][1,4]oxazepine 5-4 and (1R,5S,8S)-3-(6-methoxypyridazin-4-yl)-3-azabicyclo[3.2.1]octan-8-amine 6-3, followed by a separation of the enantiomers by reverse phase chiral HPLC afforded the title products as white solids respectively 32 mg, MS (ES+) m/z: 484.3 [(M+H)+] and 34 mg, MS (ES+) m/z: 484.3 [(M+H)+].

Examples 3 and 4

(9R)-9-(2,4-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine and (9S)-9-(2,4-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine

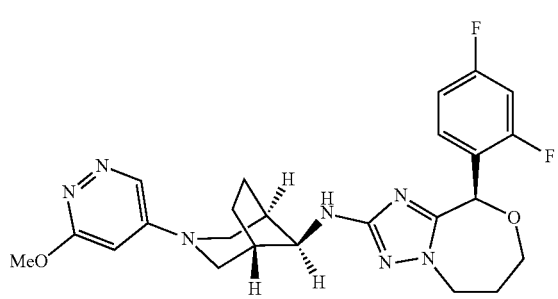

A Buchwald type coupling using the general procedure 1, between 2-bromo-9-(2,4-difluorophenyl)-5,6,7,9-tetrahydro-[1,2,4]triazolo[5,1-c][1,4]oxazepine 5-5 and (1R,5S,8S)-3-(6-methoxypyridazin-4-yl)-3-azabicyclo[3.2.1]octan-8-amine 6-3, followed by a separation of the enantiomers by reverse phase chiral HPLC afforded the title products as white solids respectively 37 mg, MS (ES+) m/z: 484.4 [(M+H)+] and 37 mg, MS (ES+) m/z: 484.4 [(M+H)+].

Examples 5 and 6

(9R)-9-(2,3-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine and (9S)-9-(2,3-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine

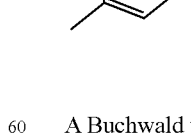
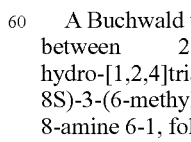

A Buchwald type coupling using the general procedure 1, between 2-bromo-9-(2,3-difluorophenyl)-5,6,7,9-tetrahydro-[1,2,4]triazolo[5,1-c][1,4]oxazepine 5-4 and (1R,5S,8S)-3-(6-methylpyrimidin-4-yl)-3-azabicyclo[3.2.1]octan-8-amine 6-1, followed by a separation of the enantiomers by reverse phase chiral HPLC afforded the title products as white solids respectively 37 mg, MS (ES+) m/z: 468.3 [(M+H)+] and 37 mg, MS (ES+) m/z: 468.3 [(M+H)+].

Examples 7 and 9

(9R)-9-(3,5-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine and (9S)-9-(3,5-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine

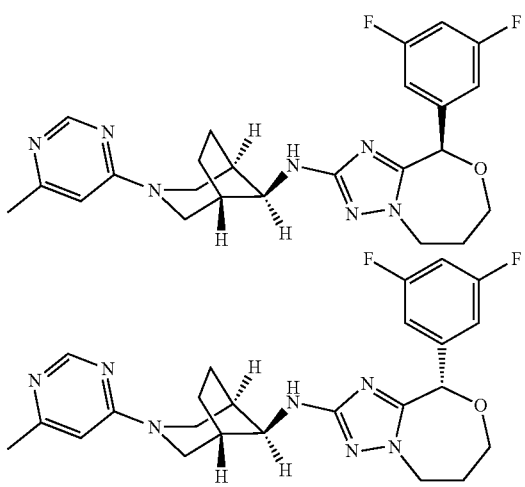

A Buchwald type coupling using the general procedure 1, between 2-bromo-9-(3,5-difluorophenyl)-5,6,7,9-tetrahydro-[1,2,4]triazolo[5,1-c][1,4]oxazepine 5-6 and (1R,5S,8S)-3-(6-methylpyrimidin-4-yl)-3-azabicyclo[3.2.1]octan-8-amine 6-1, followed by a separation of the enantiomers by reverse phase chiral HPLC afforded the title products as white solids respectively 150 mg, MS (ES+) m/z: 468.3 [(M+H)+] and 153 mg, MS (ES+) m/z: 468.3 [(M+H)+].

Examples 8 and 10

(9R)-9-(2,4-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine and (9S)-9-(2,4-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine

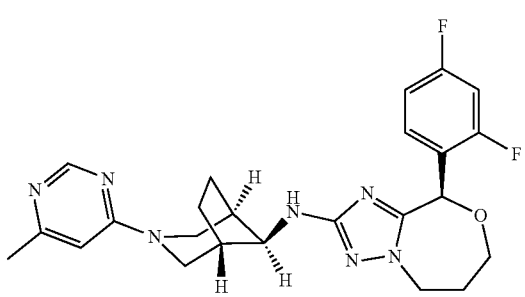

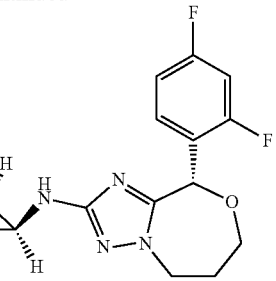

A Buchwald type coupling using the general procedure 1, between 2-bromo-9-(2,4-difluorophenyl)-5,6,7,9-tetrahydro-[1,2,4]triazolo[5,1-c][1,4]oxazepine 5-5 and (1R,5S,8S)-3-(6-methylpyrimidin-4-yl)-3-azabicyclo[3.2.1]octan-8-amine 6-1, followed by a separation of the enantiomeres by reverse phase chiral HPLC afforded the title products as white solids respectively 19.7 mg, MS (ES+) m/z: 468.3 [(M+H)+] and 18.3 mg, MS (ES+) m/z: 468.2 [(M+H)+].

Examples 11 and 12

(9R)-9-(3,5-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine and (9S)-9-(3,5-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine

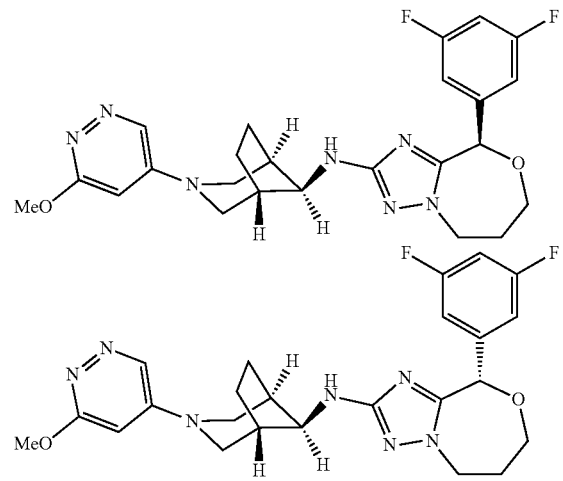

A Buchwald type coupling using the general procedure 1, between 2-bromo-9-(3,5-difluorophenyl)-5,6,7,9-tetrahydro-[1,2,4]triazolo[5,1-c][1,4]oxazepine 5-6 and (1R,5S,8S)-3-(6-methoxypyridazin-4-yl)-3-azabicyclo[3.2.1]octan-8-amine 6-3, followed by a separation of the enantiomers by reverse phase chiral HPLC afforded the title products as white solids respectively 17.3 mg, MS (ES+) m/z: 484.3 [(M+H)+] and 18.9 mg, MS (ES+) m/z: 484.3 [(M+H)+].

Examples 13 and 14

(9R)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine and (9S)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine

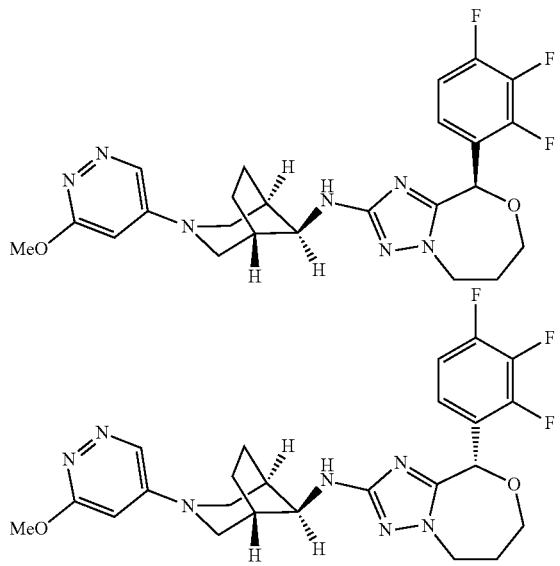

A Buchwald type coupling using the general procedure 1, between 2-bromo-9-(2,3,4-trifluorophenyl)-5,6,7,9-tetrahydro-[1,2,4]triazolo[5,1-c][1,4]oxazepine 5-7 and (1R,5S,8S)-3-(6-methoxypyridazin-4-yl)-3-azabicyclo[3.2.1]octan-8-amine 6-3, followed by a separation of the enantiomers by reverse phase chiral HPLC afforded the title products as white solids respectively 12.2 mg, MS (ES+) m/z: 502.3 [(M+H)$^+$] and 16.9 mg, MS (ES+) m/z: 502.3 [(M+H)$^+$].

Examples 15 and 16

(9R)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine and (9S)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine

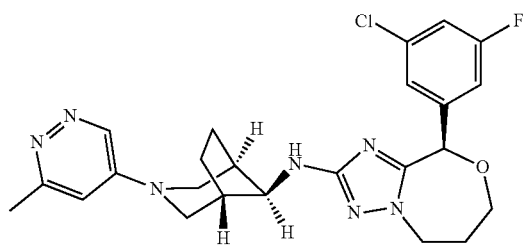

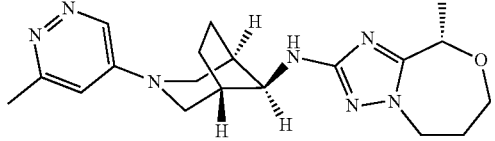
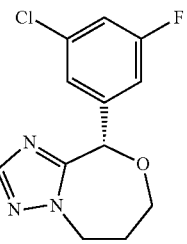

A Buchwald type coupling using the general procedure 1, between 2-bromo-9-(3-chloro-5-fluoro-phenyl)-5,6,7,9-tetrahydro-[1,2,4]triazolo[5,1-c][1,4]oxazepine 5-3 and (1R,5S,8S)-3-(6-methylpyridazin-4-yl)-3-azabicyclo[3.2.1]octan-8-amine 6-4, followed by a separation of the enantiomers by reverse phase chiral HPLC afforded the title products as white solids respectively 102 mg, MS (ES+) m/z: 484.3 [(M+H)$^+$] and 82.9 mg, MS (ES+) m/z: 484.3 [(M+H)$^+$].

Examples 17 and 18

(9R)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine and (9S)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine

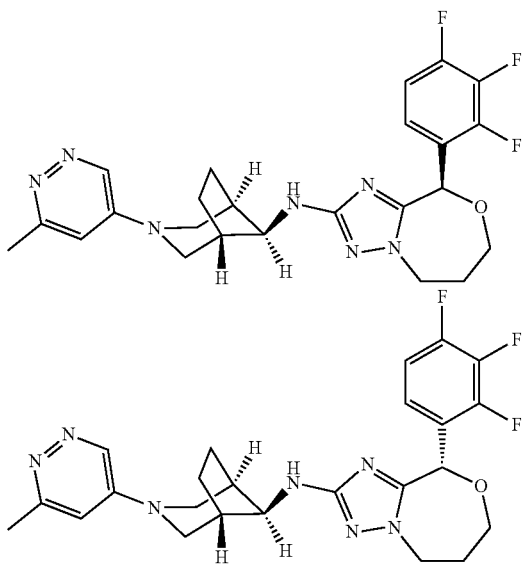

A Buchwald type coupling using the general procedure 1, between 2-bromo-9-(2,3,4-trifluorophenyl)-5,6,7,9-tetrahydro-[1,2,4]triazolo[5,1-c][1,4]oxazepine 5-7 and (1R,5S,8S)-3-(6-methylpyridazin-4-yl)-3-azabicyclo[3.2.1]octan-8-amine 6-4, followed by a separation of the enantiomers by reverse phase chiral HPLC afforded the title products as white solids respectively 17 mg, MS (ES+) m/z: 486.3 [(M+H)$^+$] and 16 mg, MS (ES+) m/z: 486.3 [(M+H)$^+$].

Examples 19 and 20

(9R)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine and (9S)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine

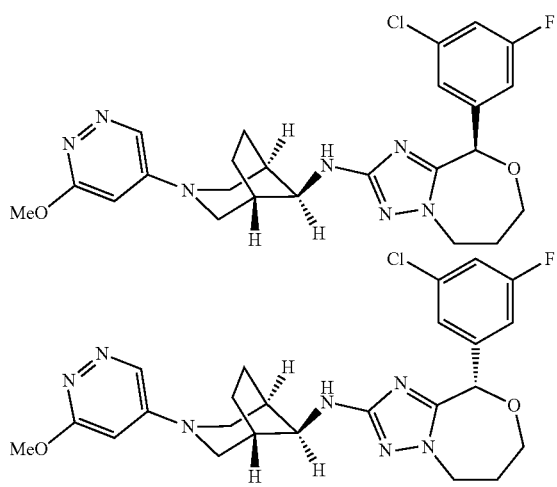

A Buchwald type coupling using the general procedure 1, between 2-bromo-9-(3-chloro-5-fluoro-phenyl)-5,6,7,9-tetrahydro-[1,2,4]triazolo[5,1-c][1,4]oxazepine 5-3 and (1R,5S,8S)-3-(6-methoxypyridazin-4-yl)-3-azabicyclo[3.2.1]octan-8-amine 6-3, followed by a separation of the enantiomers by reverse phase chiral HPLC afforded the title products as white solids respectively 37 mg, MS (ES+) m/z: 500.3 [(M+H)$^+$] and 40 mg, MS (ES+) m/z: 500.3 [(M+H)$^+$].

Examples 21 and 22

(8R)-8-(3-chloro-5-fluoro-phenyl)-N-[(1R,5S)-3-(6-methoxypyridazin-4-yl)-3-azabicyclo[3.2.1]octan-8-yl]-6,8-dihydro-5H-[1,2,4]triazolo[5,1-c][1,4]oxazin-2-amine and (8S)-8-(3-chloro-5-fluoro-phenyl)-N-[(1R,5S)-3-(6-methoxypyridazin-4-yl)-3-azabicyclo[3.2.1]octan-8-yl]-6,8-dihydro-5H-[1,2,4]triazolo[5,1-c][1,4]oxazin-2-amine

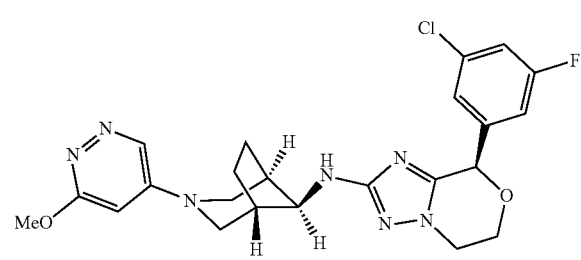

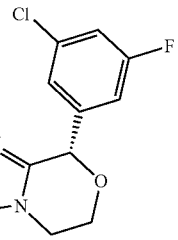

A Buchwald type coupling using the general procedure 1, between 2-bromo-8-(3-chloro-5-fluoro-phenyl)-6,8-dihydro-5H-[1,2,4]triazolo[5,1-c][1,4]oxazine 5-2 and (1R,5S,8S)-3-(6-methoxypyridazin-4-yl)-3-azabicyclo[3.2.1]octan-8-amine 6-3, followed by a separation of the enantiomers by reverse phase chiral HPLC afforded the title products as white solids respectively 39 mg, MS (ES+) m/z: 486.3 [(M+H)$^+$] and 36 mg, MS (ES+) m/z: 486.3 [(M+H)$^+$].

Examples 23 and 24

(8R)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine and (8S)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine

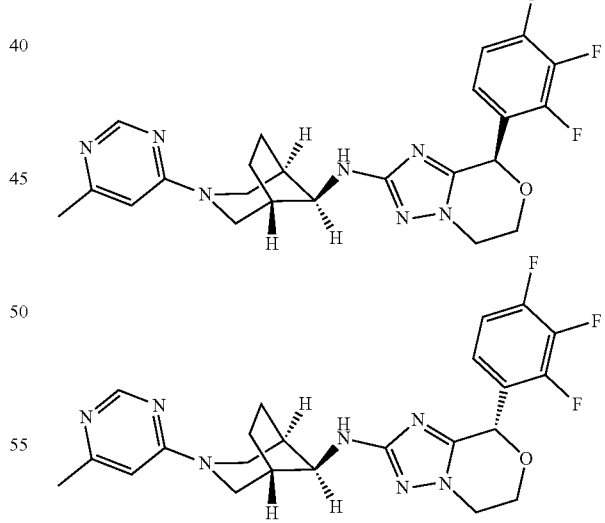

A Buchwald type coupling using the general procedure 1, between 2-bromo-8-(2,3,4-trifluorophenyl)-6,8-dihydro-5H-[1,2,4]triazolo[5,1-c][1,4]oxazine 5-1 and (1R,5S,8S)-3-(6-methylpyrimidin-4-yl)-3-azabicyclo[3.2.1]octan-8-amine 6-1, followed by a separation of the enantiomers by reverse phase chiral HPLC afforded the title products as white solids respectively 21 mg, MS (ES+) m/z: 472.3 [(M+H)$^+$] and 25 mg, MS (ES+) ink: 472.3 [(M+H)$^+$].

Examples 25 and 26

(8R)-8-(3-chloro-5-fluoro-phenyl)-N-[(1R,5S)-3-(6-methylpyrimidin-4-yl)-3-azabicyclo[3.2.1]octan-8-yl]-6,8-dihydro-5H-[1,2,4]triazolo[5,1-c][1,4]oxazin-2-amine and (8S)-8-(3-chloro-5-fluoro-phenyl)-N-[(1R,5S)-3-(6-methylpyrimidin-4-yl)-3-azabicyclo[3.2.1]octan-8-yl]-6,8-dihydro-5H-[1,2,4]triazolo[5,1-c][1,4]oxazin-2-amine

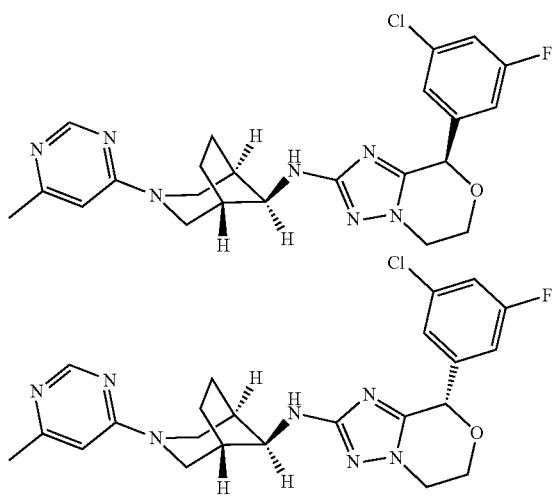

A Buchwald type coupling using the general procedure 1, between 2-bromo-8-(3-chloro-5-fluoro-phenyl)-6,8-dihydro-5H-[1,2,4]triazolo[5,1-c][1,4]oxazine 5-2 and (1R,5S,8S)-3-(6-methylpyrimidin-4-yl)-3-azabicyclo[3.2.1]octan-8-amine 6-1, followed by a separation of the enantiomeres by reverse phase chiral HPLC afforded the title products as white solids respectively 8 mg, MS (ES+) m/z: 470.2 [(M+H)$^+$] and 9 mg, MS (ES+) m/z: 470.2 [(M+H)$^+$].

Examples 27 and 28

(8R)—N-[(1R,5S)-3-(6-methoxypyridazin-4-yl)-3-azabicyclo[3.2.1]octan-8-yl]-8-(2,3,4-trifluorophenyl)-6,8-dihydro-5H-[1,2,41]triazolo[5,1-c][1,4]oxazin-2-amine and (8S)—N-[(1R,5S)-3-(6-methoxypyridazin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine

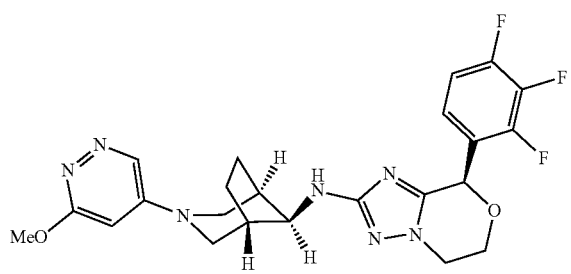

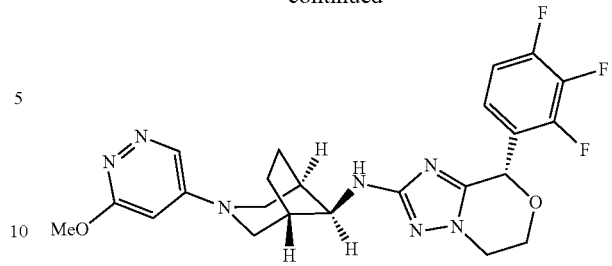

A Buchwald type coupling using the general procedure 1, between 2-bromo-8-(2,3,4-trifluorophenyl)-6,8-dihydro-5H-[1,2,4]triazolo[5,1-c][1,4]oxazine 5-1 and (1R,5S,8S)-3-(6-methoxypyridazin-4-yl)-3-azabicyclo[3.2.1]octan-8-amine 6-3, followed by a separation of the enantiomers by reverse phase chiral HPLC afforded the title products as white solids respectively 26 mg, MS (ES+) m/z: 488.3 [(M+H)$^+$] and 26 mg, MS (ES+) m/z: 488.3 [(M+H)$^+$].

Examples 29 and 30

(8R)-8-(3-chloro-5-fluoro-phenyl)-N-[(1R,5S)-3-(2-methoxy-4-pyridyl)-3-azabicyclo[3.2.1]octan-8-yl]-6,8-dihydro-5H-[1,2,4]triazolo[5,1-c][1,4]oxazin-2-amine and (8S)-8-(3-chloro-5-fluoro-phenyl)-N-[(1R,5S)-3-(2-methoxy-4-pyridyl)-3-azabicyclo[3.2.1]octan-8-yl]-6,8-dihydro-5H-[1,2,4]triazolo[5,1-c][1,4]oxazin-2-amine

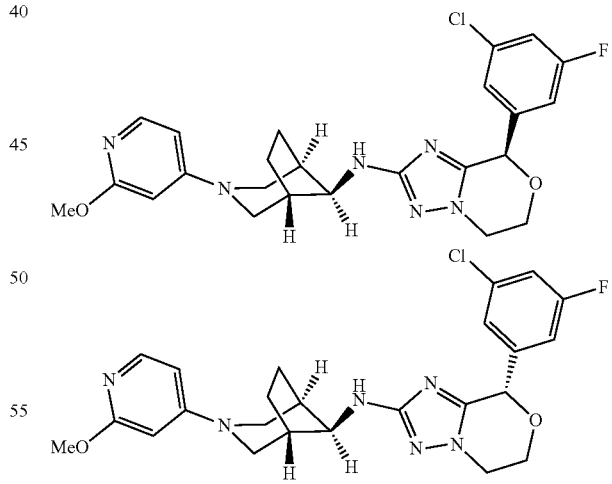

A Buchwald type coupling using the general procedure 1, between 2-bromo-8-(3-chloro-5-fluoro-phenyl)-6,8-dihydro-5H-[1,2,4]triazolo[5,1-c][1,4]oxazine 5-2 and (1R,5S,8S)-3-(2-methoxy-4-pyridyl)-3-azabicyclo[3.2.1]octan-8-amine 6-2, followed by a separation of the enantiomers by reverse phase chiral HPLC afforded the title products as white solids respectively 13 mg, MS (ES+) m/z: 486.3 [(M+H)$^+$] and 14 mg, MS (ES+) m/z: 486.2 [(M+H)$^+$].

Examples 31 and 32

(8R)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine and (8S)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine

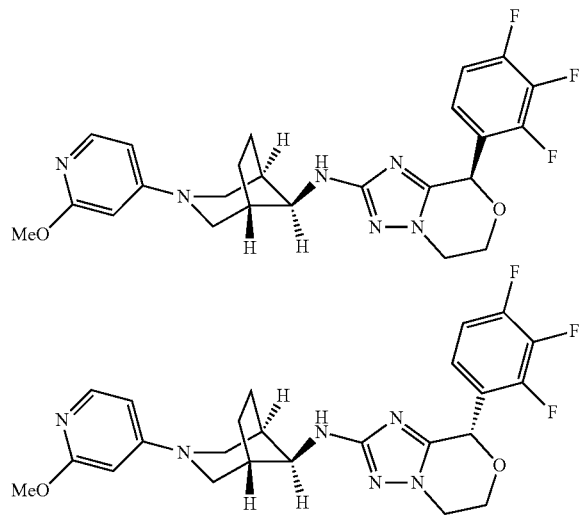

A Buchwald type coupling using the general procedure 1, between 2-bromo-8-(2,3,4-trifluorophenyl)-6,8-dihydro-5H-[1,2,4]triazolo[5,1-c][1,4]oxazine 5-1 and (1R,5S,8S)-3-(2-methoxy-4-pyridyl)-3-azabicyclo[3.2.1]octan-8-amine 6-2, followed by a separation of the enantiomers by reverse phase chiral HPLC afforded the title products as white solids respectively 19 mg, MS (ES+) m/z: 488.3 [(M+H)$^+$] and 21 mg, MS (ES+) ink: 488.3 [(M+H)$^+$].

Examples 33 and 34

(9R)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine and (9S)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine

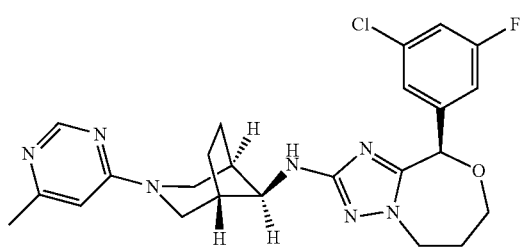

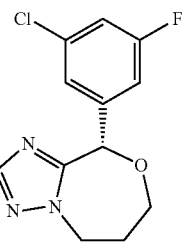

A Buchwald type coupling using the general procedure 1, between 2-bromo-9-(3-chloro-5-fluoro-phenyl)-5,6,7,9-tetrahydro-[1,2,4]triazolo[5,1-c][1,4]oxazepine 5-3 and (1R,5S,8S)-3-(6-methylpyrimidin-4-yl)-3-azabicyclo[3.2.1]octan-8-amine 6-1, followed by a separation of the enantiomers by reverse phase chiral HPLC afforded the title products as white solids respectively 34 mg, MS (ES+) m/z: 484.3 [(M+H)$^+$] and 33 mg, MS (ES+) m/z: 484.3 [(M+H)$^+$].

Example 35 and 36

(9R)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine and (9S)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine

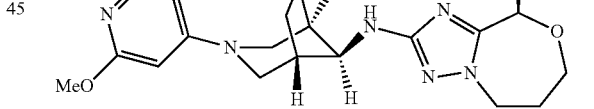
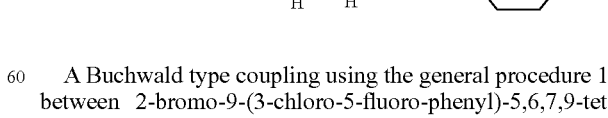

A Buchwald type coupling using the general procedure 1, between 2-bromo-9-(3-chloro-5-fluoro-phenyl)-5,6,7,9-tetrahydro-[1,2,4]triazolo[5,1-c][1,4]oxazepine 5-3 and (1R,5S,8S)-3-(2-methoxy-4-pyridyl)-3-azabicyclo[3.2.1]octan-8-amine 6-2, followed by a separation of the enantiomers by reverse phase chiral HPLC afforded the title products as white solids respectively 26 mg, MS (ES+) m/z: 499.3 [(M+H)$^+$] and 25 mg, MS (ES+) m/z: 499.3 [(M+H)$^+$].

Examples 37 and 38

(9R)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine and (9S)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine

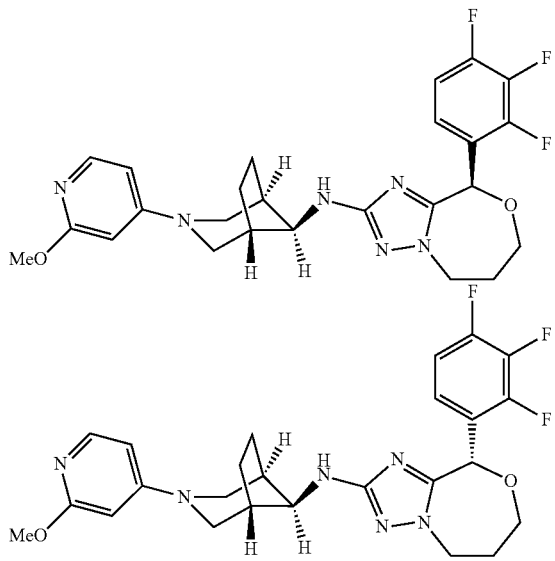

A Buchwald type coupling using the general procedure 1, between 2-bromo-9-(2,3,4-trifluorophenyl)-5,6,7,9-tetrahydro-[1,2,4]triazolo[5,1-c][1,4]oxazepine 5-7 and (1R,5S,8S)-3-(2-methoxy-4-pyridyl)-3-azabicyclo[3.2.1]octan-8-amine 6-2, followed by a separation of the enantiomers by reverse phase chiral HPLC afforded the title products as white solids respectively 28.3 mg, MS (ES+) m/z: 501.3 [(M+H)$^+$] and 26 mg, MS (ES+) m/z: 501.3 [(M+H)$^+$].

Examples 39 and 40

(9R)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine and (9S)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine

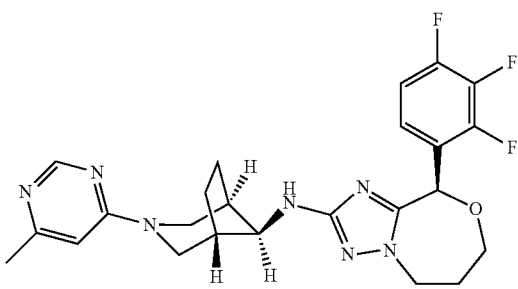

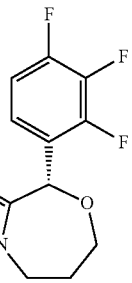

A Buchwald type coupling using the general procedure 1, between 2-bromo-9-(2,3,4-trifluorophenyl)-5,6,7,9-tetrahydro-[1,2,4]triazolo[5,1-c][1,4]oxazepine 5-7 and (1R,5S,8S)-3-(6-methylpyrimidin-4-yl)-3-azabicyclo[3.2.1]octan-8-amine 6-1, followed by a separation of the enantiomers by reverse phase chiral HPLC afforded the title products as white solids respectively 50 mg, MS (ES+) m/z: 486.3 [(M+H)$^+$] and 41 mg, MS (ES+) m/z: 486.3 [(M+H)$^+$].

2) Biological Examples

2.1) Assay Procedure: Cellular γ-Secretase Assay

Human neuroglioma H4 cells overexpressing human APP695 with the Swedish double mutation (K595N/M596L) were plated at 30,000 cells/well/100 μL in 96-well plates in IMDM containing 10% FCS, 0.2 mg/L Hygromycin B and incubated at 37° C., 5% $CO_2$. 3-4 h post plating, compounds are a diluted in media and 50 μL is added as 1.5-fold concentrate to achieve the final concentration. Compound incubation is performed for 24 h. Final doses typically range from 4 μM down to 0.0013 μM in half-log steps resulting in an eight-point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat # AL203C, Perkin Elmer). 20 μL of the cell culture supernatant was transferred to an assay plate. Then 10 μL, of a mixture of the AlphaLisa coupled capture antibody and the biotinylated detection antibody was added and incubated for 3 h at RT while softly shaking the assay plate. After a further addition of 20 μL of the Donor beads the assay plate was incubated for 30 min at RT and constant shaking without exposure to direct light. The assay plate was then read on a Paradigm AlphaLisa Reader using the build-in program with excitation at 680 nm and emission at 570 nm. The measured signals were then used to calculate $IC_{50}$ values for inhibition of Aβ42 secretion by nonlinear regression fit analysis using XLfit 5.3 software (from IDBS company).

2.2) Results

The table below shows the data for all compounds for the inhibition of Aβ42 secretion:

| Example | Aβ42 $IC_{50}$ (μM) |
| --- | --- |
| 1 | 0.0847 |
| 2 | 0.0511 |

-continued

| Example | Aβ42 IC$_{50}$ (μM) |
|---|---|
| 3 | 0.0874 |
| 4 | 0.0762 |
| 5 | 0.0477 |
| 6 | 0.0623 |
| 7 | 0.0433 |
| 8 | 0.0749 |
| 9 | 0.0217 |
| 10 | 0.0718 |
| 11 | 0.0221 |
| 12 | 0.0723 |
| 13 | 0.0218 |
| 14 | 0.0451 |
| 15 | 0.0239 |
| 16 | 0.0626 |
| 17 | 0.0823 |
| 19 | 0.0132 |
| 20 | 0.0345 |
| 21 | 0.0166 |
| 22 | 0.0718 |
| 23 | 0.0597 |
| 24 | 0.0789 |
| 25 | 0.0208 |
| 27 | 0.0774 |
| 28 | 0.0959 |
| 29 | 0.0112 |
| 31 | 0.0520 |
| 33 | 0.0109 |
| 34 | 0.0196 |
| 35 | 0.00658 |
| 36 | 0.0129 |
| 37 | 0.0157 |
| 38 | 0.0127 |
| 39 | 0.0439 |
| 40 | 0.0192 |

The invention claimed is:

1. A compound of formula (I),

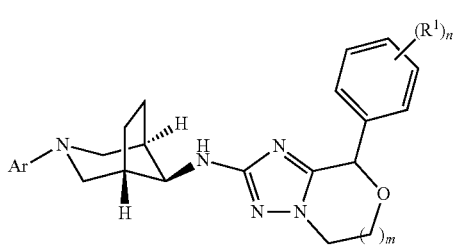

wherein:
n is 1, 2 or 3;
each $R^1$ is independently selected from halogen, lower alkyl, lower alkyl substituted by halogen, lower alkoxy, and lower alkoxy substituted by halogen;
m is 1 or 2; and
Ar is a six membered heteroaryl group, selected from:

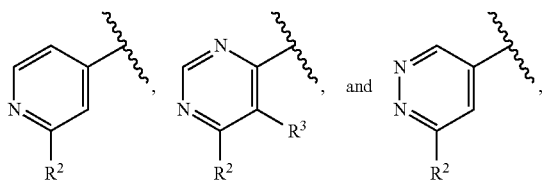

wherein:
$R^2$ is hydrogen, halogen, lower alkyl, lower alkyl substituted by halogen, or lower alkoxy; and
$R^3$ is hydrogen or halogen;
or an enantiomer, diastereomer, or a pharmaceutically acceptable salt thereof.

2. The compound of formula (I) according to claim 1, wherein the compound of formula (I) is a compound of formula (Ia):

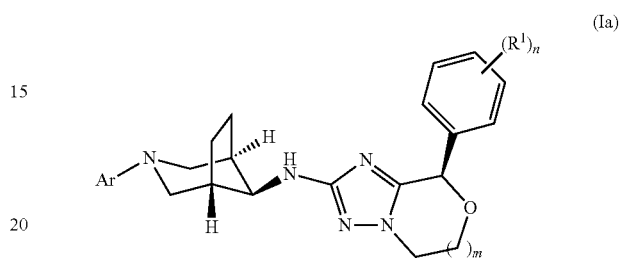

wherein $R^1$, m, n and Ar are as defined in claim 1.

3. The compound of formula (I) according to claim 1, wherein the compound of formula (I) is a compound of formula (Ib):

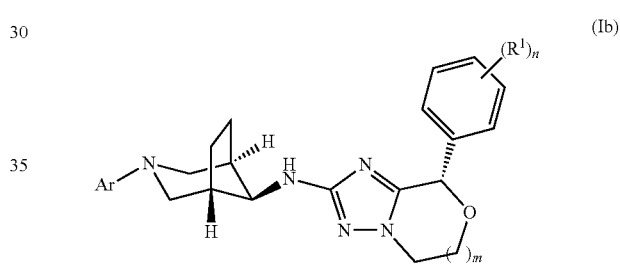

wherein $R^1$, m, n and Ar are as defined in claim 1.

4. The compound of formula (I) according to claim 1, wherein $R^1$ is halogen.

5. The compound of formula (I) according to claim 1, wherein $R^1$ is fluorine or chlorine.

6. The compound of formula (I) according to claim 1, wherein n is 2 or 3.

7. The compound of formula (I) according to claim 1, wherein Ar is a six membered heteroaryl group, selected from:

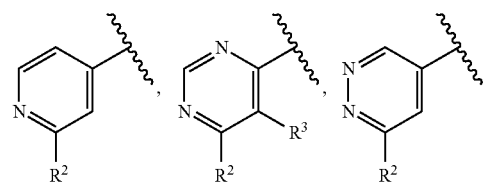

wherein:
$R^2$ is lower alkyl or lower alkoxy; and
$R^3$ is hydrogen.

8. The compound of formula (I) according to claim 1, wherein Ar is a six membered heteroaryl group, selected from:

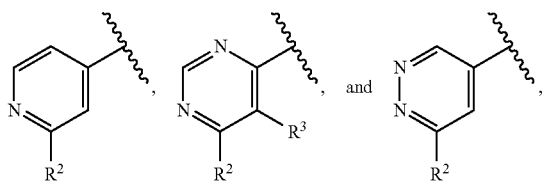

wherein:
R² is methyl or methoxy; and
R³ is hydrogen.

9. The compound of formula (I) according to claim 1, wherein:
R¹ is halogen;
n is 2 or 3;
Ar is a six membered heteroaryl group, selected from:

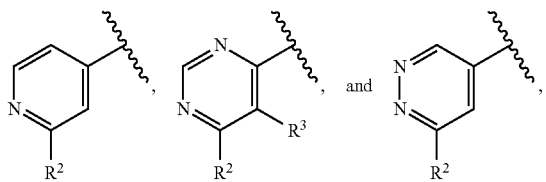

wherein:
R² is lower alkyl or lower alkoxy; and
R³ is hydrogen.

10. The compound of formula (I) according to claim 1, wherein:
R¹ is fluorine or chlorine;
n is 2 or 3; and
Ar is a six membered heteroaryl group, selected from:

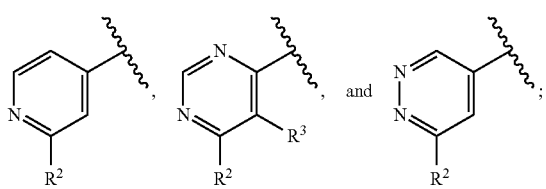

wherein:
R² is methyl or methoxy;
R³ is hydrogen.

11. A compound according to claim 1, selected from:
(9R)-9-(2,3-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,3-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9R)-9-(2,4-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,4-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9R)-9-(2,3-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,3-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(3,5-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3,5-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(2,4-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(2,4-difluorophenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(3,5-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3,5-difluorophenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9R)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9R)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;
(9R)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9R)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(8R)-8-(3-chloro-5-fluoro-phenyl)-N-[(1R,5S)-3-(6-methoxypyridazin-4-yl)-3-azabicyclo[3.2.1]octan-8-yl]-6,8-dihydro-5H-[1,2,4]triazolo[5,1-c][1,4]oxazin-2-amine;
(8S)-8-(3-chloro-5-fluoro-phenyl)-N-[(1R,5S)-3-(6-methoxypyridazin-4-yl)-3-azabicyclo[3.2.1]octan-8-yl]-6,8-dihydro-5H-[1,2,4]triazolo[5,1-c][1,4]oxazin-2-amine;
(8R)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(8S)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(8R)-8-(3-chloro-5-fluoro-phenyl)-N-[(1R,5S)-3-(6-methylpyrimidin-4-yl)-3-azabicyclo[3.2.1]octan-8-yl]-6,8-dihydro-5H-[1,2,4]triazolo[5,1-c][1,4]oxazin-2-amine;
(8S)-8-(3-chloro-5-fluoro-phenyl)-N-[(1R,5S)-3-(6-methylpyrimidin-4-yl)-3-azabicyclo[3.2.1]octan-8-yl]-6,8-dihydro-5H-[1,2,4]triazolo[5,1-c][1,4]oxazin-2-amine;
(8R)—N-[(1R,5S)-3-(6-methoxypyridazin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(8S)—N-[(1R,5S)-3-(6-methoxypyridazin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;

(8R)-8-(3-chloro-5-fluoro-phenyl)-N-[(1R,5S)-3-(2-methoxy-4-pyridyl)-3-azabicyclo[3.2.1]octan-8-yl]-6,8-dihydro-5H-[1,2,4]triazolo[5,1-c][1,4]oxazin-2-amine;
(8S)-8-(3-chloro-5-fluoro-phenyl)-N-[(1R,5S)-3-(2-methoxy-4-pyridyl)-3-azabicyclo[3.2.1]octan-8-yl]-6,8-dihydro-5H-[1,2,4]triazolo[5,1-c][1,4]oxazin-2-amine;
(8R)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(8S)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(9R)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;
(9R)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9R)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine; and
(9S)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

or a pharmaceutically acceptable salt thereof.

12. A compound according to claim 1, selected from:
(9R)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methoxypyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9R)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(6-methylpyridazin-4-yl)-3-azabicyclo[3.2.1]octan-8-yl]-5,6,7,9-tetrahydro-[1,2,4]triazolo[5,1-c][1,4]oxazepin-2-amine;
(9R)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methylpyridazin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9R)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(6-methoxypyridazin-4-yl)-3-azabicyclo[3.2.1]octan-8-yl]-5,6,7,9-tetrahydro-[1,2,4]triazolo[5,1-c][1,4]oxazepin-2-amine;
(8R)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(8S)—N-[(1R,5S)-3-(6-methylpyrimidin-4-yl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(8R)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(8S)—N-[(1R,5S)-3-(2-methoxy-4-pyridyl)-3-azabicyclo[3.2.1]octan-8-yl]-8-(2,3,4-trifluorophenyl)-6,8-dihydro-5H-[1,2,4]triazolo[5,1-c][1,4]oxazin-2-amine;
(9R)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(6-methylpyrimidin-4-yl)-3-azabicyclo[3.2.1]octan-8-yl]-5,6,7,9-tetrahydro-[1,2,4]triazolo[5,1-c][1,4]oxazepin-2-amine;
(9R)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;
(9S)-9-(3-chloro-5-fluoro-phenyl)-N-[(1R,5S)-3-(2-methoxy-4-pyridyl)-3-azabicyclo[3.2.1]octan-8-yl]-5,6,7,9-tetrahydro-[1,2,4]triazolo[5,1-c][1,4]oxazepin-2-amine;
(9R)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(2-methoxy-4-pyridyl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9R)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;
(9S)—N-[(1R,5S)-3-(6-methylpyrimidin-4-yl)-3-azabicyclo[3.2.1]octan-8-yl]-9-(2,3,4-trifluorophenyl)-5,6,7,9-tetrahydro-[1,2,4]triazolo[5,1-c][1,4]oxazepin-2-amine;

or a pharmaceutically acceptable salt thereof.

13. A process for preparing a compound of formula (I) according to claim 1 or a pharmaceutically acceptable salt thereof, the process comprising:

reacting a compound 5

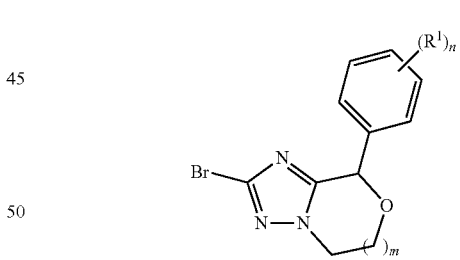

with an amine 6

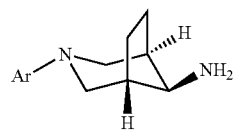

wherein Ar, $R^1$, n and m are as defined in claim 1, to form the compound of formula (I); and optionally converting the compound into a pharmaceutically acceptable salt thereof.

14. A pharmaceutical composition comprising a compound according to claim 1 and a therapeutically inert carrier.

15. A method for the therapeutic and/or prophylactic treatment of Alzheimer's disease, cerebral amyloid angiopathy, hereditary cerebral hemorrhage with amyloidosis-Dutch type, multi-infarct dementia, dementia pugilistica, or Down syndrome, which method comprises: administering an effective amount of a compound as defined in claim 1 to a patient in need thereof.

16. A pharmaceutical composition comprising a compound according to claim 11 and a therapeutically inert carrier.

17. A pharmaceutical composition comprising a compound according to claim 12 and a therapeutically inert carrier.

18. A method for the therapeutic and/or prophylactic treatment of Alzheimer's disease, cerebral amyloid angiopathy, hereditary cerebral hemorrhage with amyloidosis-Dutch type, multi-infarct dementia, dementia pugilistica, or Down syndrome, which method comprises:
   administering an effective amount of a compound as defined in claim 11 to a patient in need thereof.

19. A method for the therapeutic and/or prophylactic treatment of Alzheimer's disease, cerebral amyloid angiopathy, hereditary cerebral hemorrhage with amyloidosis-Dutch type, multi-infarct dementia, dementia pugilistica, or Down syndrome, which method comprises:
   administering an effective amount of a compound as defined in claim 12 to a patient in need thereof.

* * * * *